US012169929B2

(12) United States Patent
Ogawa et al.

(10) Patent No.: US 12,169,929 B2
(45) Date of Patent: Dec. 17, 2024

(54) INFORMATION PROCESSING APPARATUS AND INFORMATION PROCESSING METHOD

(71) Applicant: SONY GROUP CORPORATION, Tokyo (JP)

(72) Inventors: Sayaka Ogawa, Tokyo (JP); Kota Aizawa, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 491 days.

(21) Appl. No.: 17/430,869

(22) PCT Filed: Jan. 10, 2020

(86) PCT No.: PCT/JP2020/000666
§ 371 (c)(1),
(2) Date: Aug. 13, 2021

(87) PCT Pub. No.: WO2020/170645
PCT Pub. Date: Aug. 27, 2020

(65) Prior Publication Data
US 2022/0084196 A1   Mar. 17, 2022

(30) Foreign Application Priority Data

Feb. 22, 2019   (JP) ................... 2019-030102

(51) Int. Cl.
*G06T 7/00* (2017.01)
*A63F 13/213* (2014.01)
*G06V 40/16* (2022.01)

(52) U.S. Cl.
CPC .......... *G06T 7/0012* (2013.01); *A63F 13/213* (2014.09); *G06V 40/168* (2022.01); *G06V 40/174* (2022.01); *A63F 2300/1087* (2013.01)

(58) Field of Classification Search
CPC ................. G06T 7/0012; A63F 13/213; A63F 2300/1087; A63F 13/212; G06V 40/168;
(Continued)

(56) References Cited

U.S. PATENT DOCUMENTS

| 2003/0108241 A1 | 6/2003 | Colmenarez et al. |
| 2018/0107275 A1* | 4/2018 | Chen ........ G06F 3/015 |

FOREIGN PATENT DOCUMENTS

| CN | 1602620 A | 3/2005 |
| JP | 2005-512248 A | 4/2005 |

(Continued)

OTHER PUBLICATIONS

Translation of WO 2017/006872 A1 (Year: 2024).*
International Search Report and Written Opinion of PCT Application No. PCT/JP2020/000666, issued on Mar. 17, 2020, 10 pages of ISRWO.

*Primary Examiner* — Peter J Iannuzzi
(74) *Attorney, Agent, or Firm* — CHIP LAW GROUP

(57) ABSTRACT

A configuration that analyzes reflection light of light emitted to a user face and executes both facial-expression analysis and biometric-signal analysis together is realized. The configuration has a light-receiving section that receives reflection light of light emitted to a user face, and a light-reception-signal analyzing section that analyzes a light-reception signal of the light-receiving section. The light-reception-signal analyzing section has a facial-expression analyzing section that analyzes user-skin-surface reflection light and generates facial-expression analysis information, and a biometric-signal analyzing section that analyzes subepidermal reflection light and generates bioanalysis information. The light-reception signal of the light-receiving section includes skin-surface reflection light and subepidermal-tissue reflection light, and the facial-expression analyzing section extracts a low frequency component from the light-reception signal, acquires the skin-surface reflection (Continued)

light, and executes facial-expression analysis. The biometric-signal analyzing section extracts a high frequency component from the light-reception signal, acquires the subepidermal-tissue reflection light, and executes a biometric-signal analysis process.

19 Claims, 28 Drawing Sheets

(58) Field of Classification Search
CPC .... G06V 40/174; G06V 40/166; A61B 5/022; A61B 5/0245; A61B 5/026; A61B 5/107; A61B 5/1455; A61B 5/16
See application file for complete search history.

(56) References Cited

FOREIGN PATENT DOCUMENTS

| | | | | |
|---|---|---|---|---|
| JP | 2008-131405 A | 6/2008 | | |
| JP | 2013-150772 A | 8/2013 | | |
| JP | 2017-021737 A | 1/2017 | | |
| KR | 10-2004-0068210 A | 7/2004 | | |
| WO | 03/051033 A1 | 6/2003 | | |
| WO | 2016/165052 A1 | 10/2016 | | |
| WO | WO-2017006872 A1 * | 1/2017 | ............... | G06F 3/01 |

* cited by examiner

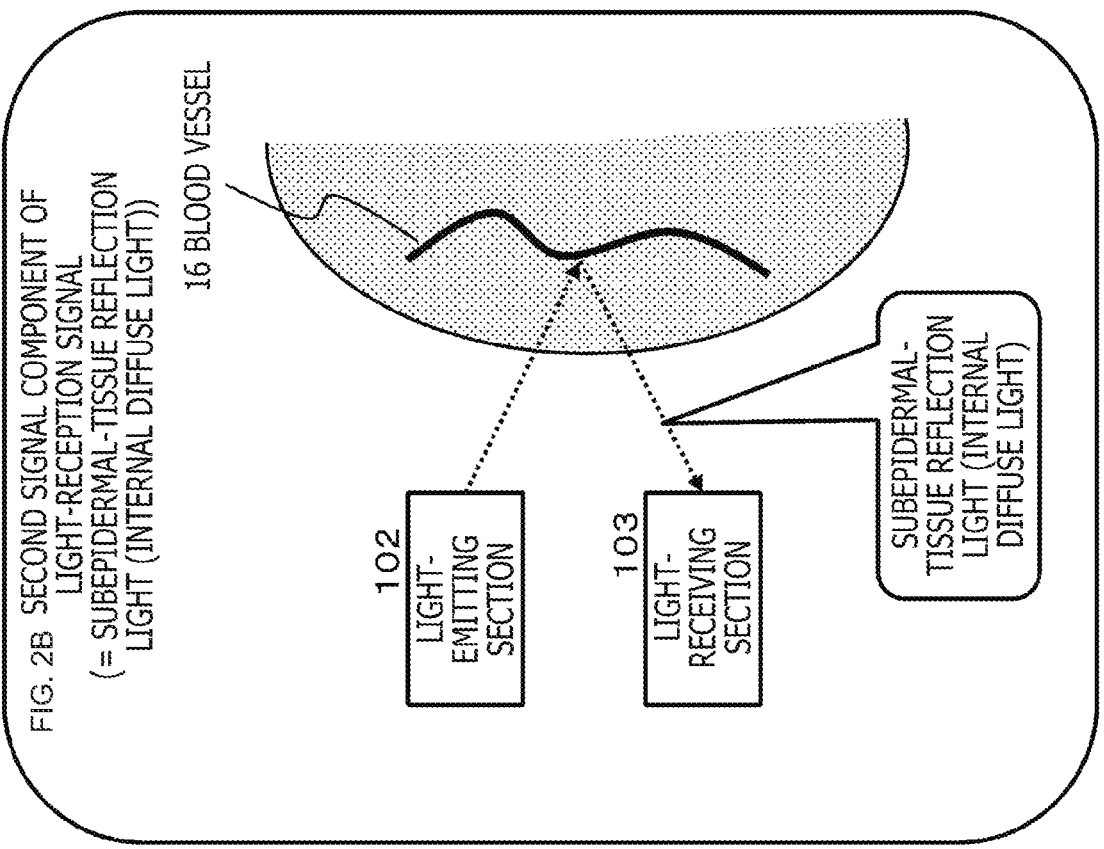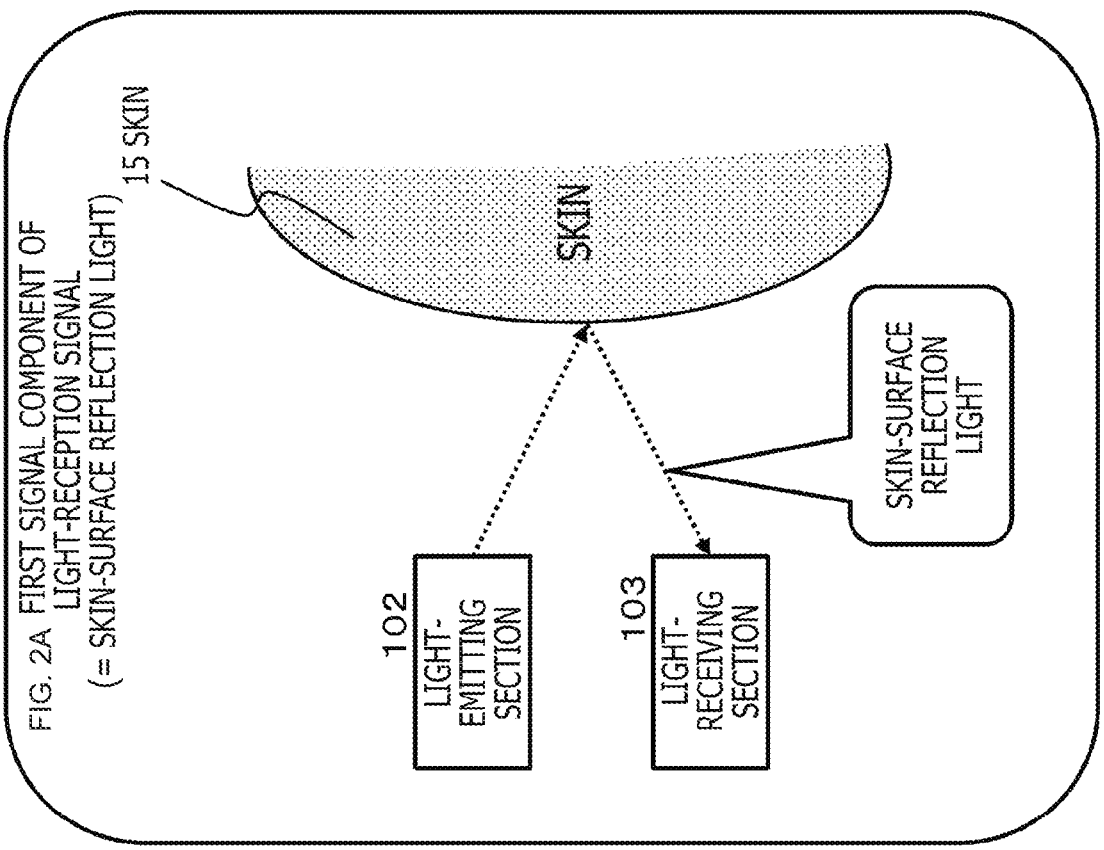

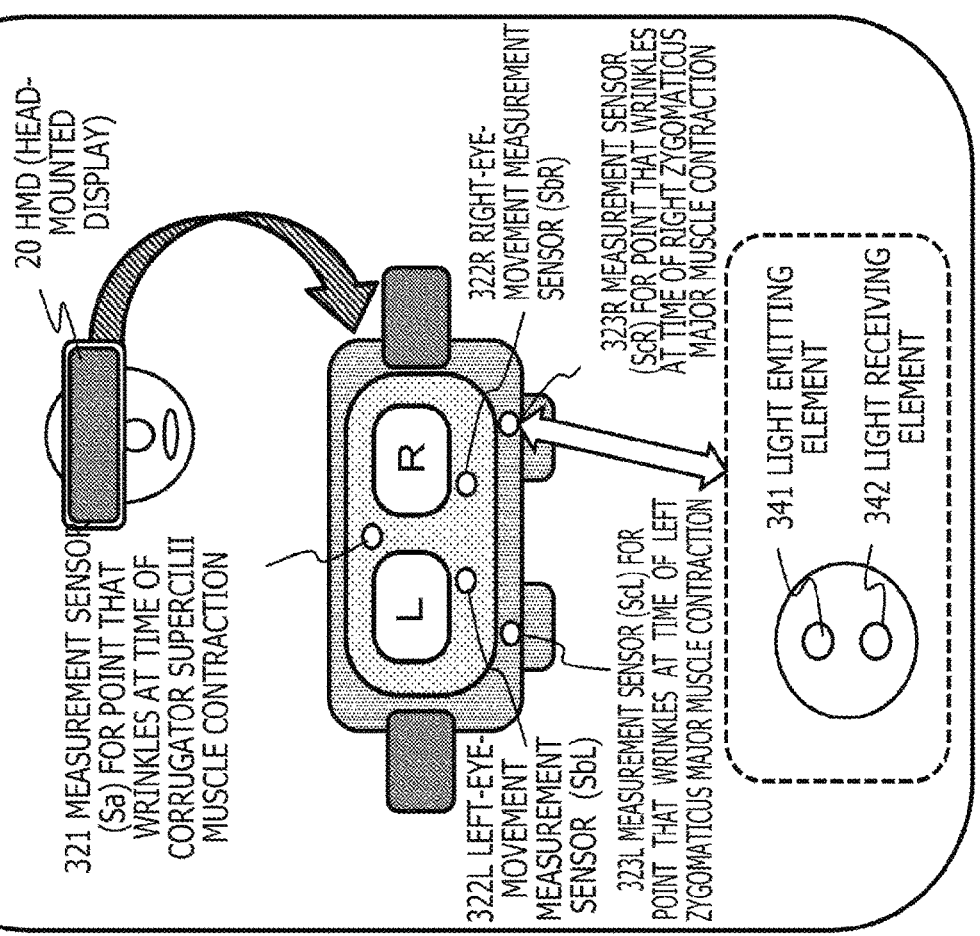
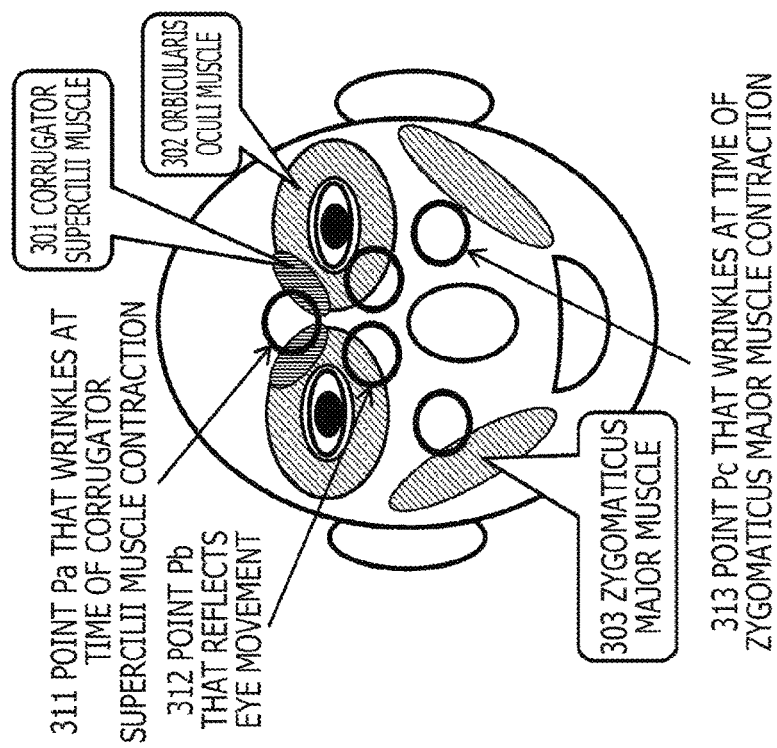

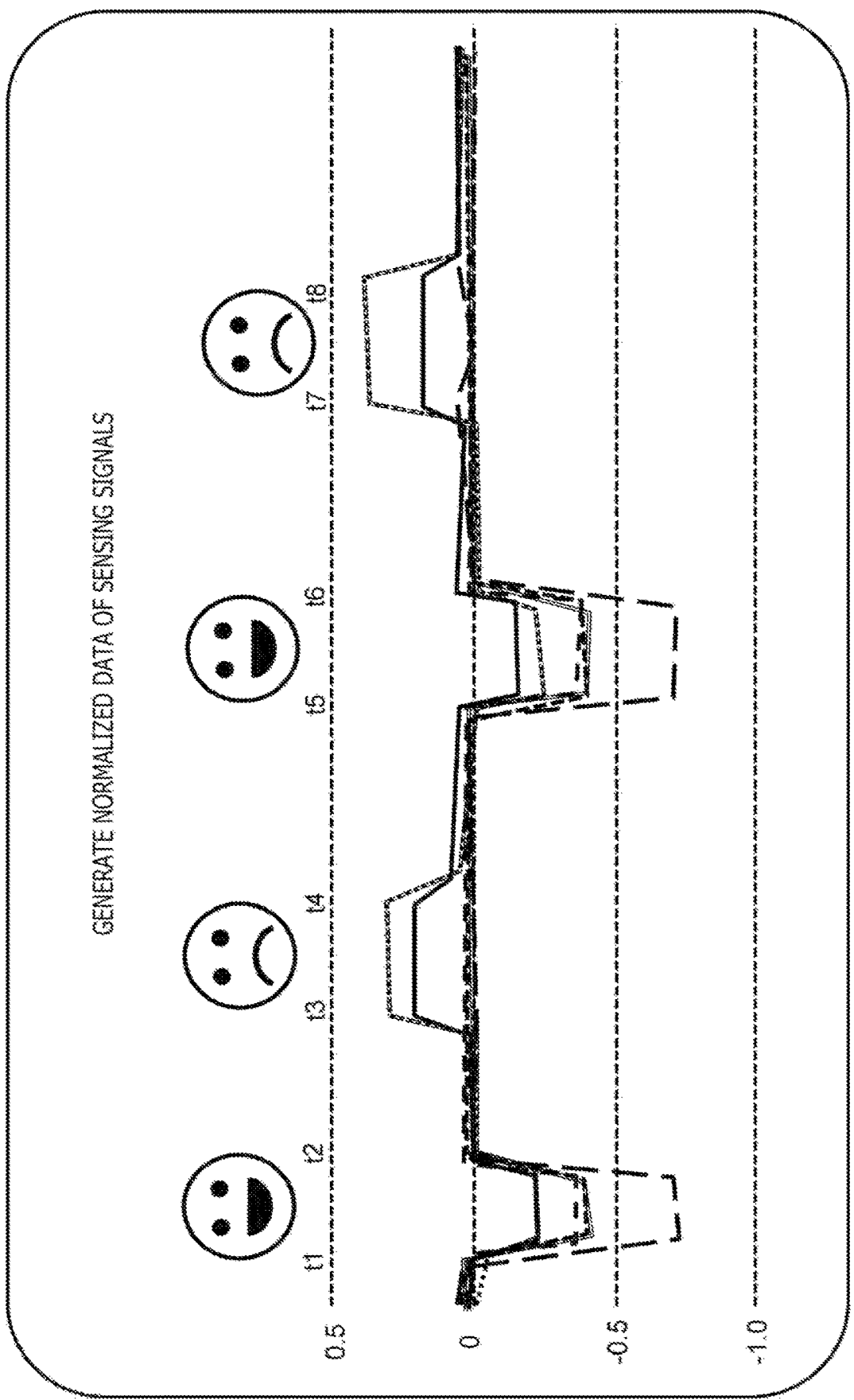

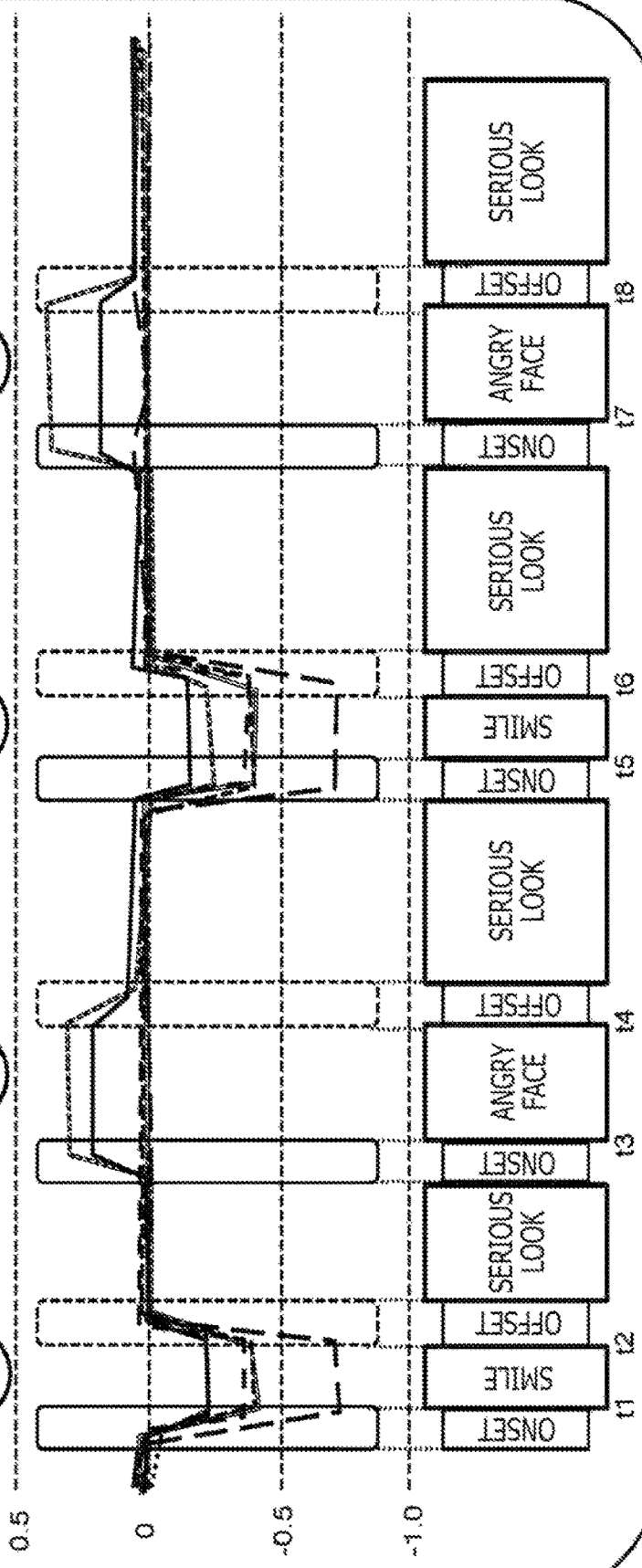

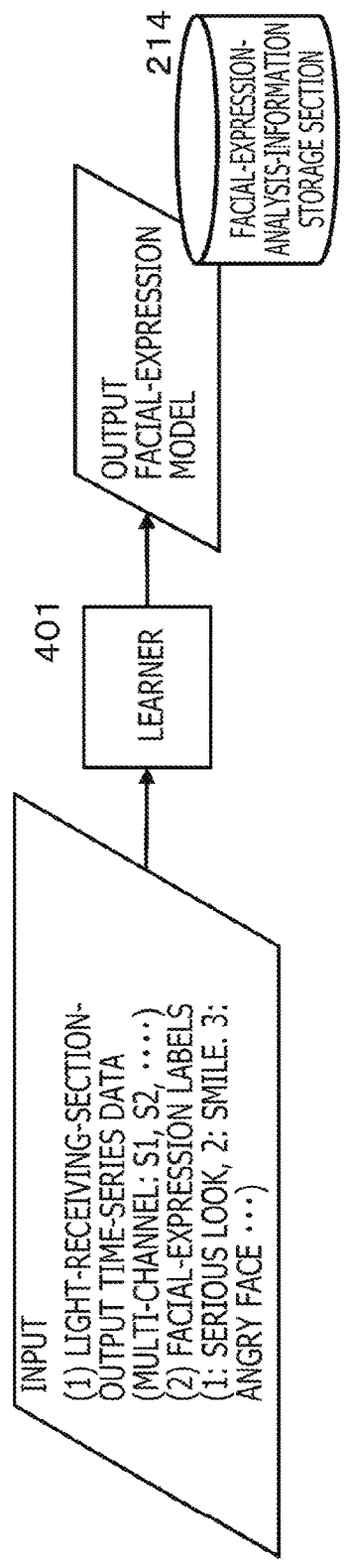
FIG. 13A  AT TIME OF LEARNING
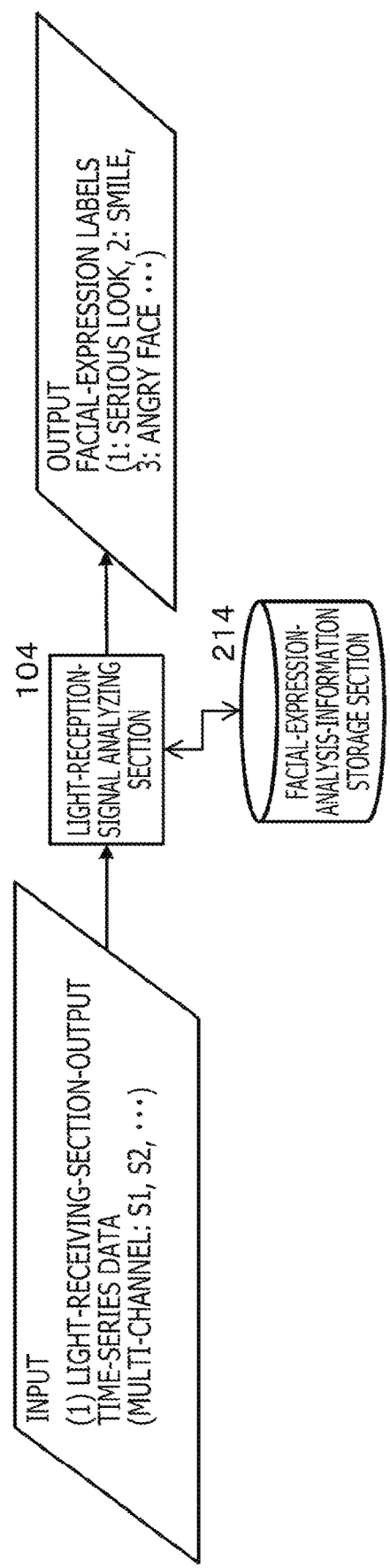
FIG. 13B  AT TIME OF EXECUTION OF FACIAL-EXPRESSION ANALYSIS PROCESS

FIG. 14

SPECIFIC EXAMPLE OF LEARNING PROCESS
USE EXAMPLE OF HIDDEN MARKOV MODEL (HMM): DATA OF USER
FACIAL EXPRESSIONS IS COLLECTED TO CONSTRUCT LEARNING MODEL (S01) AN ONSET PERIOD IS SET BY AUTOMATIC or MANUAL SEGMENTATION, AND A LABEL IS GIVEN TO THE ONSET PERIOD. A USER IS INSTRUCTED BY A SYSTEM BY BEING TOLD, "SHOW ME A SMILE NOW," ETC., AND VISUALLY PRESENTS A FACIAL EXPRESSION. WHEN THE VARIANCE OF MEASUREMENT SIGNALS IN THE LATEST PERIOD OF 0.2 SECONDS EXCEEDS A THRESHOLD, IT IS DEEMED THAT THERE IS A FACIAL-EXPRESSION CHANGE FROM A SERIOUS LOOK TO A SMILE, AND THE PERIOD IS SET AS AN ONSET PERIOD BY SEGMENTATION.

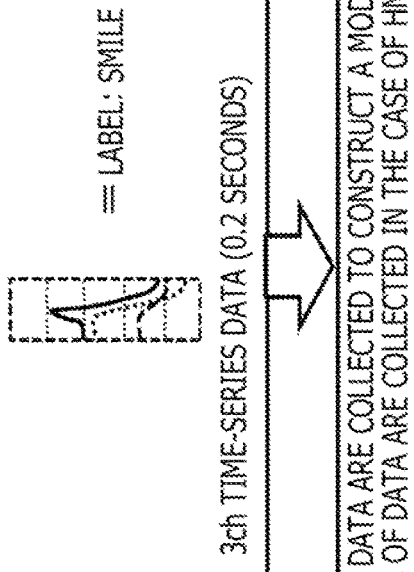

= LABEL: SMILE

3ch TIME-SERIES DATA (0.2 SECONDS)

(S02) A PLURALITY OF PIECES OF DATA ARE COLLECTED TO CONSTRUCT A MODEL (APPROXIMATELY 3 TO 10 PIECES OF DATA ARE COLLECTED IN THE CASE OF HMM)

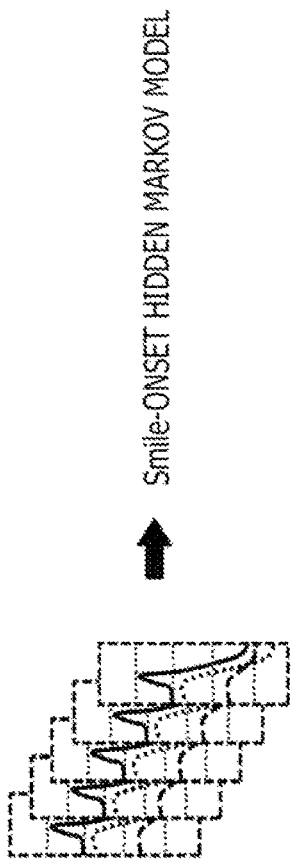

Smile-ONSET HIDDEN MARKOV MODEL

FIG. 15

SPECIFIC EXAMPLE OF FACIAL-EXPRESSION ANALYSIS PROCESS

USE EXAMPLE OF HIDDEN MARKOV MODEL (HMM): EXAMPLE OF ANALYSIS BY USING LEARNING MODEL (HIDDEN MARKOV MODEL)

(PROCESS) AN INFORMATION PROCESSING APPARATUS THAT EXECUTES USER-FACIAL-EXPRESSION ANALYSIS ACQUIRES ACQUISITION SIGNALS OF SENSORS THAT SENSE REFLECTION LIGHT OF THE USER FACIAL SKIN. FURTHER, DATA IN A PERIOD THAT IS ESTIMATED AS BEING AN ONSET PERIOD IS RETRIEVED ON THE BASIS OF ANALYSIS DATA, FOR EXAMPLE, THE VARIANCE, CORRESPONDING TO THE ACQUISITION SIGNALS. FURTHER, THE LIKELIHOOD OF THE RETRIEVED DATA AND FEATURE DATA CORRESPONDING TO EACH FACIAL-EXPRESSION LABEL IN A LEARNING MODEL (FACIAL-EXPRESSION MODEL) IS COMPUTED. LAST, A FACIAL-EXPRESSION LABEL SET CORRESPONDING TO FEATURE DATA WITH HIGH LIKELIHOOD (WITH A HIGH SIMILARITY) IS DETERMINED AS A USER FACIAL EXPRESSION.

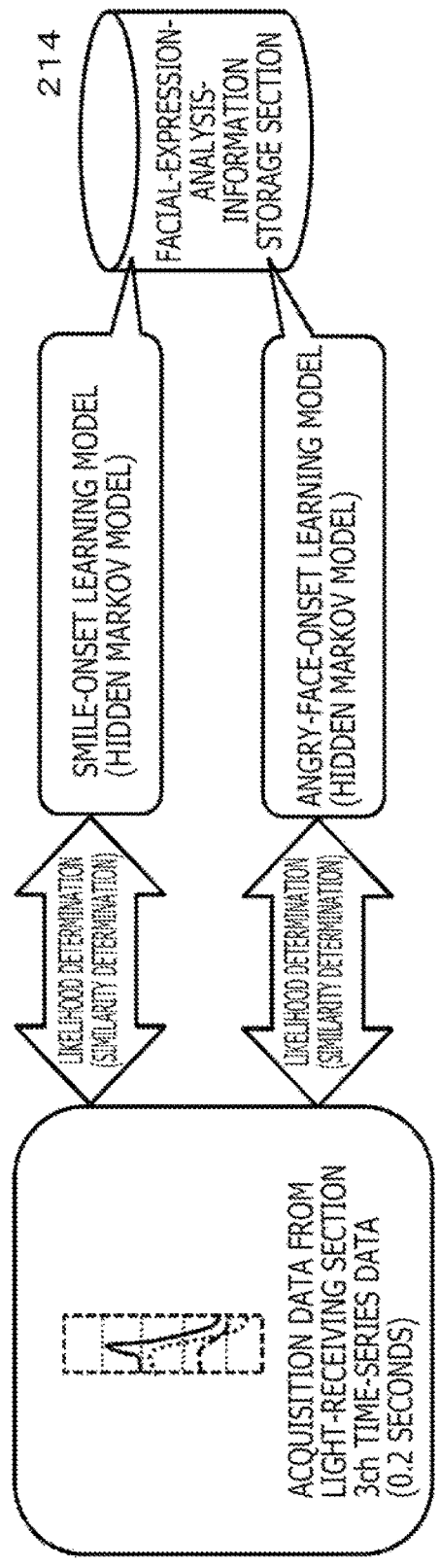

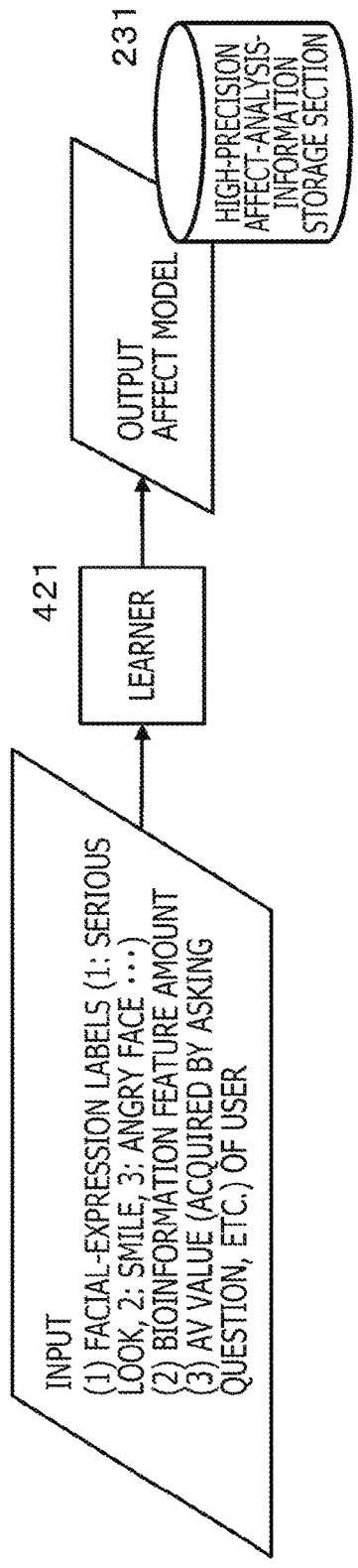
FIG. 21A  AT TIME OF LEARNING
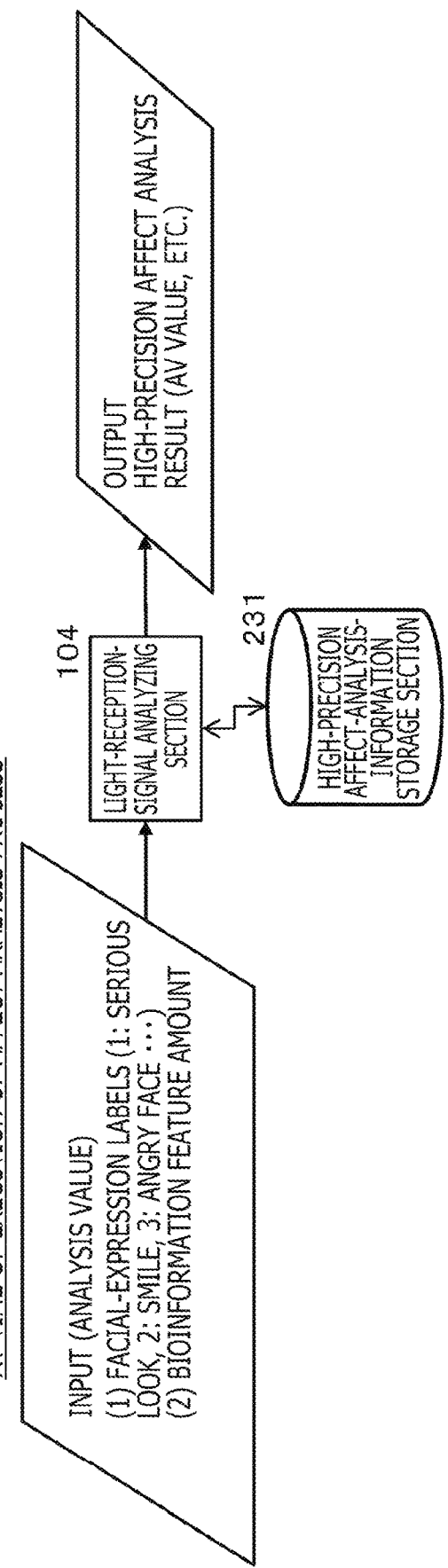
FIG. 21B  AT TIME OF EXECUTION OF AFFECT ANALYSIS PROCESS

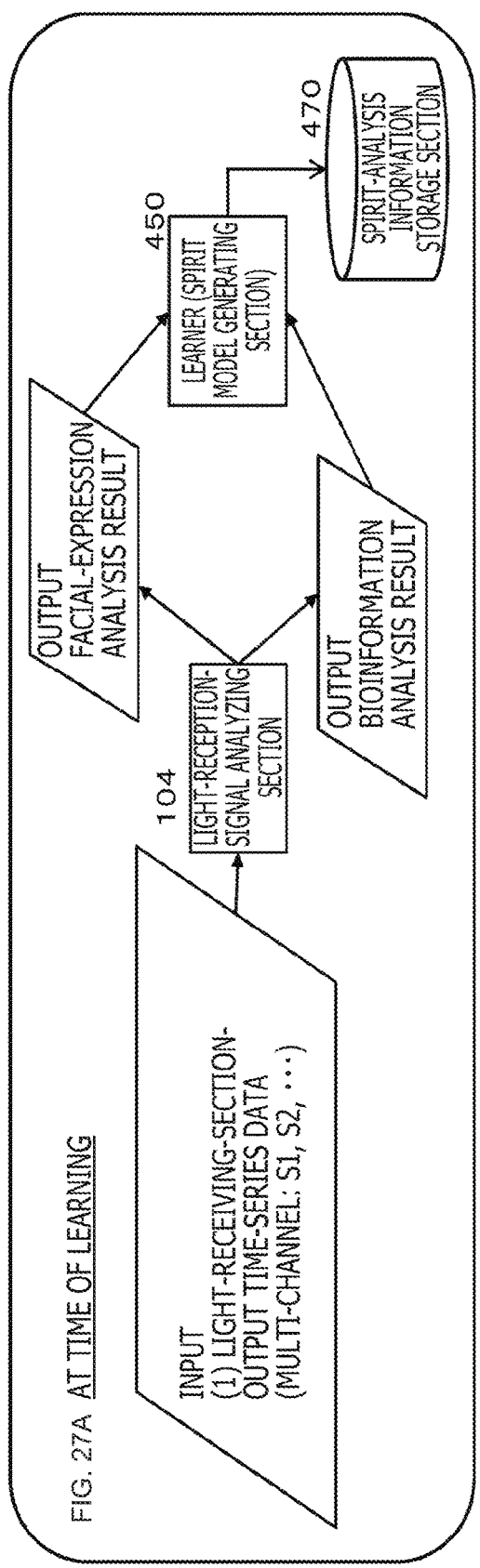
FIG. 27A AT TIME OF LEARNING
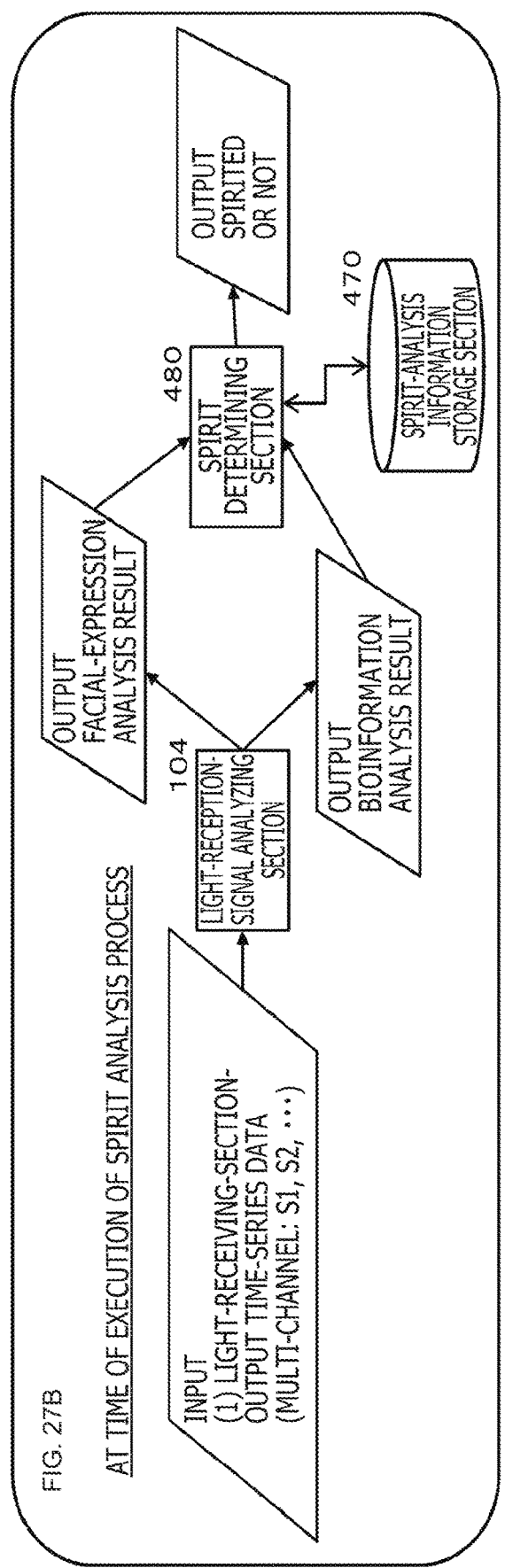
FIG. 27B AT TIME OF EXECUTION OF SPIRIT ANALYSIS PROCESS

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2020/000666 filed on Jan. 10, 2020, which claims priority benefit of Japanese Patent Application No. JP 2019-030102 filed in the Japan Patent Office on Feb. 22, 2019. Each of the above-referenced applications is hereby incorporated herein by reference in its entirety.

TECHNICAL FIELD

The present disclosure relates to an information processing apparatus, an information processing method, and a program. More specifically, the present disclosure relates to an information processing apparatus, an information processing method, and a program which human facial-expression analysis and bioanalysis are executed.

BACKGROUND ART

As processes of analyzing a human facial expression, there are known processes of analyzing an image captured by a camera to thereby analyze whether or not there is a smile on the image, for example.

Note that conventional technologies that disclose technologies of analyzing a facial expression of a face on an image captured by a camera include one that is disclosed in PTL (JP 2008-131405A), for example.

Further, there is also a known technology of performing bioanalysis of a human, which is what is called vital sensing, by analyzing the blood flow state, components, and the like of blood vessels of the human.

For example, PTL 2 (JP 2013-150772A) discloses a configuration to perform a bioanalysis process based on optical signals.

In such a manner, various studies have conventionally been conducted about a facial-expression analysis process and a bioanalysis processes, but there is none that discloses a configuration that executes those two analysis processes together, on the basis of sensing information of one sensor.

CITATION LIST

Patent Literature

[PTL 1]
  JP 2008-131405A
[PTL 2]
  JP 2013-150772A

SUMMARY

Technical Problem

There has been a problem that, in a case where the conventional technologies described above are used in combination, it is necessary to arrange a plurality of sensors in order to acquire both facial-expression information and bioinformation, and it becomes difficult to realize a wearable apparatus in terms of a physical shape, weight, power consumption, and the like. In addition, there has also been a problem that, if it is attempted to acquire both facial-expression information and bioinformation from one location on a face, sensors for acquiring both types of information interfere with each other, and it becomes difficult to perform appropriate sensing.

The present disclosure has been made in view of the problems described above, for example, and an object of the present disclosure is to provide an information processing apparatus, an information processing method, and a program that make it possible to execute a facial-expression analysis process and a bioanalysis process together on the basis of sensing information of one sensor.

Solution to Problem

A first aspect of the present disclosure resides in an information processing apparatus including a light-receiving section that receives reflection light of light emitted to a user face, and a light-reception-signal analyzing section that analyzes a light-reception signal of the light-receiving section. The light-reception-signal analyzing section has a facial-expression analyzing section that generates facial-expression analysis information on the basis of the reflection light, and a biometric-signal analyzing section that generates bioanalysis information on the basis of the reflection light.

Further, a second aspect of the present disclosure resides in an information processing method executed at an information processing apparatus. The information processing apparatus includes a light-receiving section that receives reflection light of light emitted to a user face, and a light-reception-signal analyzing section that analyzes a light-reception signal of the light-receiving section. The light-reception-signal analyzing section executes a facial-expression analysis process of generating facial-expression analysis information on the basis of the reflection light. The light-reception-signal analyzing section executes a biometric-signal analysis process of generating bioanalysis information on the basis of the reflection light.

Further, a third aspect of the present disclosure resides in a program that causes information processing to be executed at an information processing apparatus. The information processing apparatus includes a light-receiving section that receives reflection light of light emitted to a user face, and a light-reception-signal analyzing section that analyzes a light-reception signal of the light-receiving section. The program causes the light-reception-signal analyzing section to execute a facial-expression analysis process of generating facial-expression analysis information on the basis of the reflection light and a biometric-signal analysis process of generating bioanalysis information on the basis of the reflection light.

Note that, for example, the program of the present disclosure is a program that can be provided on a storage medium or a communication medium that provides, in a computer-readable format, various program codes to an information processing apparatus or a computer system that can execute the various program codes. By providing such a program in the computer-readable format, processes corresponding to the program are realized on the information processing apparatus or the computer system.

Still other objects, features, and merits of the present disclosure will become apparent from more detailed explanations based on embodiments and attached figures of the present disclosure mentioned below. Note that, in the present specification, a system is a logical set configuration of a plurality of apparatuses, but is not limited to one having apparatuses of individual configurations that are located in a single housing.

According to the configuration of one embodiment of the present disclosure, a configuration that analyzes reflection light of light emitted to a user face and executes both facial-expression analysis and biometric-signal analysis together is realized.

Specifically, for example, the configuration has a light-receiving section that receives reflection light of light emitted to a user face, and a light-reception-signal analyzing section that analyzes a light-reception signal of the light-receiving section. The light-reception-signal analyzing section has a facial-expression analyzing section that analyzes user-skin-surface reflection light and that generates facial-expression analysis information, and a biometric-signal analyzing section that analyzes subepidermal reflection light and that generates bioanalysis information. The light-reception signal of the light-receiving section includes skin-surface reflection light and subepidermal-tissue reflection light. The facial-expression analyzing section extracts a low frequency component from the light-reception signal, acquires the skin-surface reflection light, and executes facial-expression analysis. The biometric-signal analyzing section extracts a high frequency component from the light-reception signal, acquires the subepidermal-tissue reflection light, and executes a biometric-signal analysis process.

According to this configuration, a configuration that analyzes reflection light of light emitted to a user face and executes both facial-expression analysis and biometric-signal analysis together is realized.

Note that advantages described in the present specification are illustrated merely as examples, and advantages of the present disclosure are not limited to them. There may also be additional advantages.

BRIEF DESCRIPTION OF DRAWINGS

FIGS. 2A and 2B are figures for explaining a process executed by the information processing apparatus of the present disclosure.

FIGS. 8A and 8B are figures for explaining a sensor configuration example of the information processing apparatus of the present disclosure.

FIG. 11 is a figure for explaining a process executed by the light-reception-signal analyzing section of the information processing apparatus of the present disclosure.

FIG. 12 is a figure for explaining a process executed by the light-reception-signal analyzing section of the information processing apparatus of the present disclosure.

FIGS. 13A and 13B are figures for explaining a learning process and an analysis process executed by the information processing apparatus of the present disclosure.

FIG. 14 is a figure for explaining a learning process and an analysis process executed by the information processing apparatus of the present disclosure.

FIG. 15 is a figure for explaining a learning process and an analysis process executed by the information processing apparatus of the present disclosure.

FIGS. 21A and 21B are figures for explaining a learning process and an analysis process executed by the information processing apparatus of the present disclosure.

FIGS. 27A and 27B are figures for explaining a learning process and an analysis process executed by the information processing apparatus of the present disclosure.

DESCRIPTION OF EMBODIMENTS

Hereinafter, details of an information processing apparatus, an information processing method, and a program of the present disclosure are explained with reference to the figures. Note that explanations are given according to the following items.

1. About Overview of Processes Executed by Information Processing Apparatus of Present Disclosure
2. About Detailed Configuration and Processes of Light-Reception-Signal Analyzing Section 3. About Setting Example of Reflection-Light Measurement Points and Specific Configuration Example of Sensors 4. About Configuration and Processes for Realizing Highly Precise Facial-Expression Analysis Process 5. About Specific Example of Bioinformation Analysis Process 6. About Embodiment of Execution of Highly Precise Affect Estimation Process 7. About Use Examples of Results of Analysis by Information Processing Apparatus of Present Disclosure 7-(1) Process Example of Use for Game Event Control 7-(2) Process Example of Use for Authenticity Determination about User Facial Expression 7-(3) Process Example of Use for Mimetic-Muscle Training by User 7-(4) Process Example of Use for Avatar Control 7-(5) Process Example of Use for Determination about User Spirit 8. About Hardware Configuration Example of Information Processing Apparatus 9. Summary of Configuration of Present Disclosure

[1. About Overview of Processes Executed by Information Processing Apparatus of Present Disclosure]

First, the overview of processes executed by an information processing apparatus of the present disclosure is explained with reference to FIG. 1 and the subsequent figures.

Figure 1:
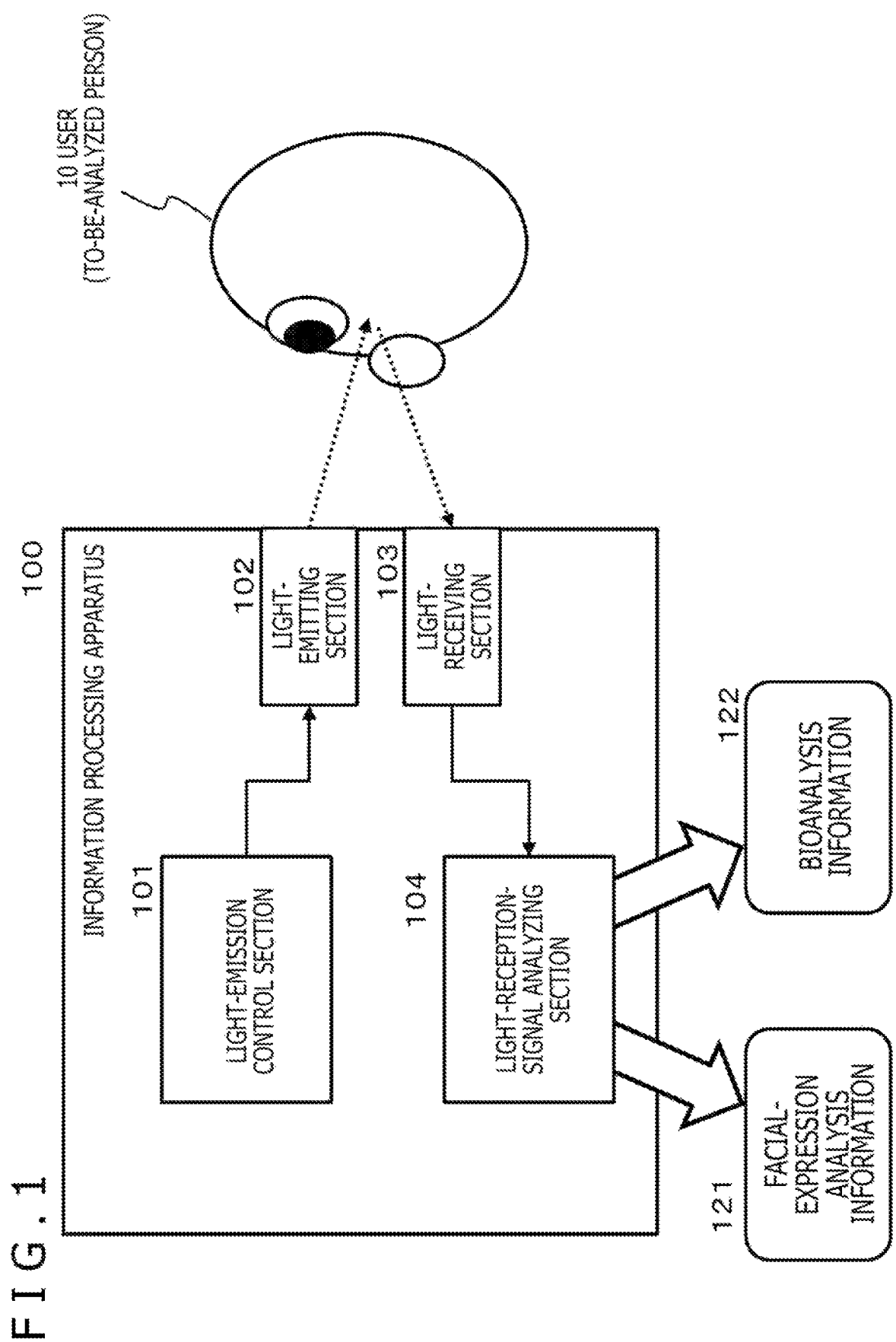
FIG. 1 is a figure for explaining a configuration example of an information processing apparatus of the present disclosure.

An information processing apparatus 100 of the present disclosure has a configuration depicted in FIG. 1.

The information processing apparatus 100 has a light-emission control section 101, a light-emitting section 102, a light-receiving sensor 103, and a light-reception-signal analyzing section 104.

The light-emission control section 101 executes light emission control of the light-emitting section 102. Output light of the light-emitting section 102 is infrared light, for example.

The output light of the light-emitting section 102 is emitted to the facial skin of a user (to-be-analyzed person) 10. The light emitted to the facial skin of the user (to-be-analyzed person) 10 is partially reflected on the skin surface and received by the light-receiving section 103.

Further, part of the output light of the light-emitting section 102 reaches subepidermal tissue, for example, blood vessels, and light reflected (diffused) by blood flowing through the blood vessels is received by the light-receiving section 103.

That is, as depicted in FIGS. 2A and 2B, a light-reception signal of the light-receiving section 103 includes the following two signal components.

FIG. 2A First signal component of light-reception signal=skin-surface reflection light FIG. 2B Second signal component of light-reception signal=subepidermal-tissue reflection light (diffuse light)

The second signal component of the light-reception signal=subepidermal-tissue reflection light (diffuse light) is reflection light (diffuse light) due to blood flowing through blood vessels, for example. The reflection light (diffuse light) due to the blood flowing through the blood vessels exhibits changes corresponding to fluctuations of the amount of blood due to blood circulation at a part irradiated with light. On the basis of the changes, the heart rate can be analyzed. In addition, the intensity of the reflection light changes corresponding to blood oxygen concentration.

By irradiating a skin surface with light and measuring temporal abnormalities of reflection light in such a manner, biometric signals such as a pulse or a blood oxygen concentration can be obtained.

In such a manner, the light-receiving section 103 receives a mixed signal of the following two types of reflection light.

(1) Skin-surface reflection light (2) Subepidermal-tissue reflection light (diffuse light)

The optical signal received by the light-receiving section 103 is output to the light-reception-signal analyzing section 104.

The light-reception-signal analyzing section 104 executes analysis of the optical signal received by the light-receiving section 103.

The light-reception-signal analyzing section 104 executes the following two processes.

(1) The light-reception-signal analyzing section 104 executes facial-expression analysis of the user (to-be-analyzed person) 10 by analysis of a skin-surface-reflection-light component and generates and outputs facial-expression analysis information 21.

For example, the light-reception-signal analyzing section 104 generates and outputs the facial-expression analysis information 21 representing that the facial expression of the user (to-be-analyzed person) 10 is a smile, a sad face, or an angered facial expression.

Further, (2) The light-reception-signal analyzing section 104 generates and outputs bioanalysis information 122 of the user (to-be-analyzed person) 10 by analysis of subepidermal-tissue reflection light (diffuse light).

For example, the light-reception-signal analyzing section 104 generates and outputs the bioanalysis information 122 such as a blood flow rate, a blood flow speed, a pulse wave, a blood pressure, a heart rate, a heart rate fluctuation, a blood oxygen concentration, or arterial oxygen saturation of the user (to-be-analyzed person) 10.

Note that the information processing apparatus 100 depicted in FIG. 1 can be included in a head-mounted display (HMD) worn by the user 10, for example.

Figure 3:
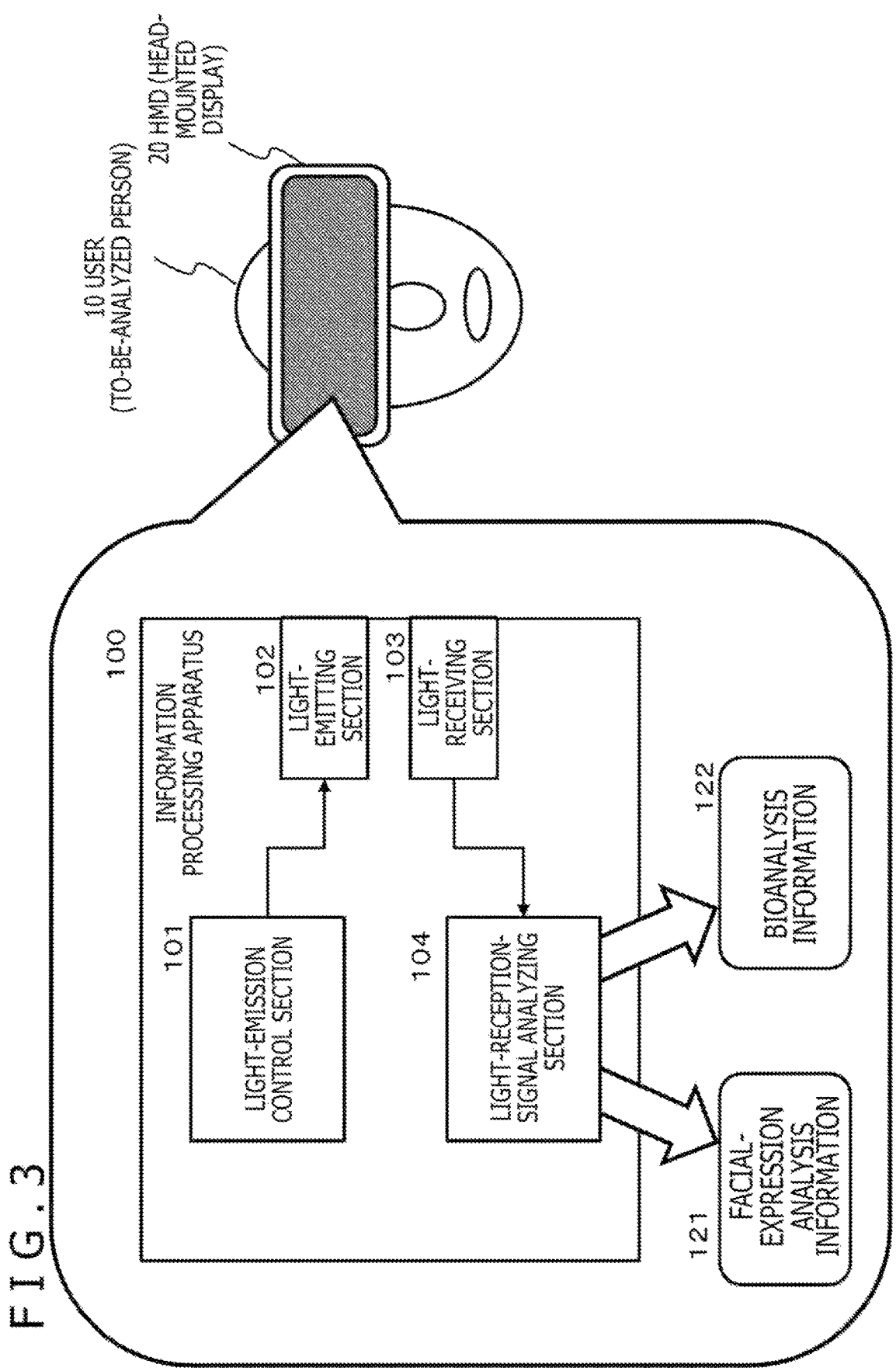
FIG. 3 is a figure for explaining a configuration example of the information processing apparatus of the present disclosure.

That is, the information processing apparatus 100 can be included in a head-mounted display (HMD) 20 worn by the user (to-be-analyzed person) 10 as depicted in FIG. 3.

Note that the head-mounted display (HMD) 20 includes therein a sensor including a plurality of pairs of light-emitting sections and light-receiving sections, and sensing information at different positions on the face of the user (to-be-analyzed person) 10 is acquired and analyzed.

Specific examples of the setting positions and analysis processes of the sensor are explained in detail in a latter section.

[2. About Detailed Configuration and Processes of Light-Reception-Signal Analyzing Section]

Next, the detailed configuration of the light-reception-signal analyzing section 104 of the information processing apparatus 100 depicted in FIG. 1 and processes to be executed by the light-reception-signal analyzing section 104 are explained.

Figure 4:
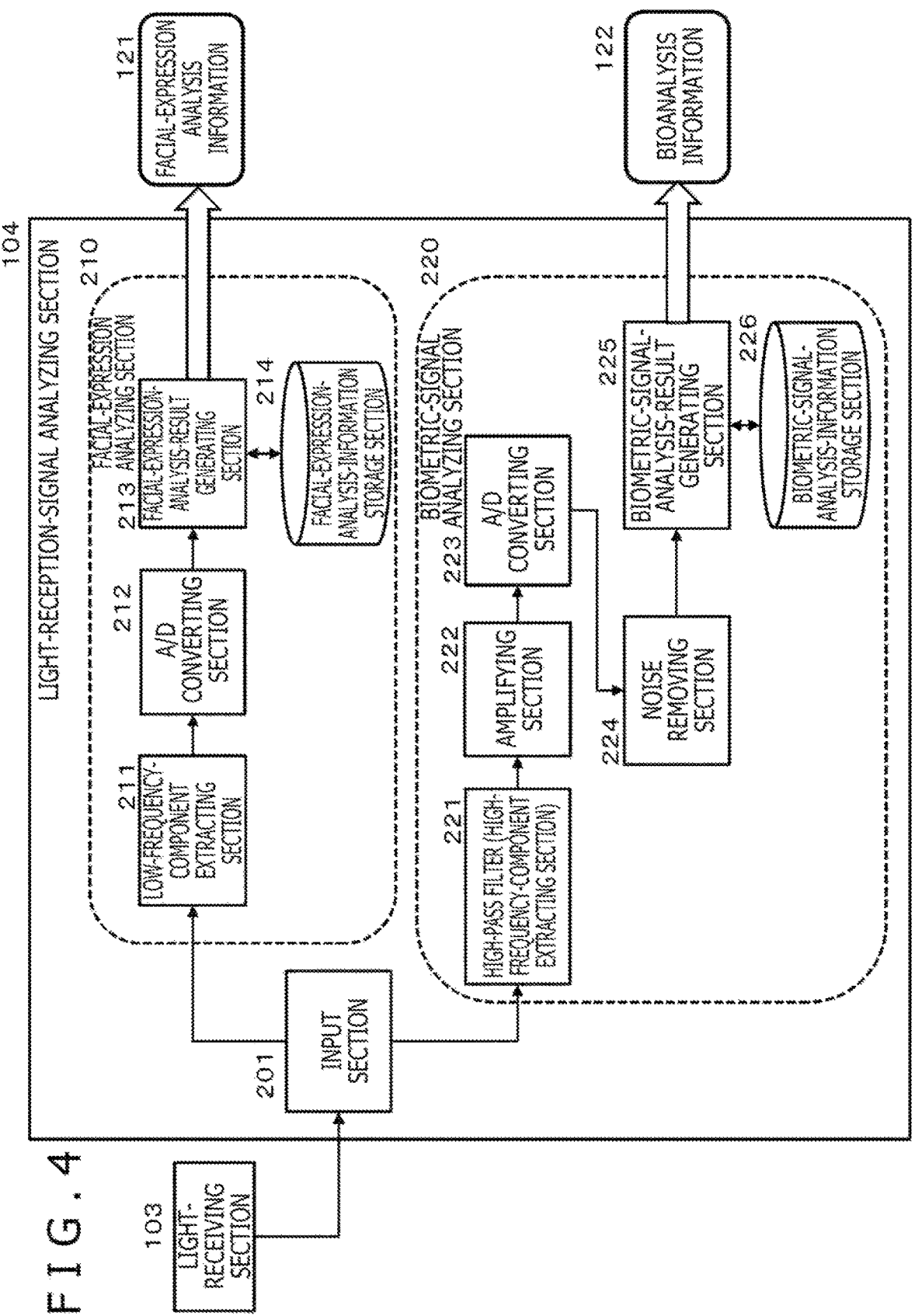
FIG. 4 is a figure for explaining a configuration example of a light-reception-signal analyzing section of the information processing apparatus of the present disclosure.

FIG. 4 is a block diagram depicting the detailed configuration of the light-reception-signal analyzing section 104 of the information processing apparatus 100 depicted in FIG. 1.

As depicted in FIG. 4, the light-reception-signal analyzing section 104 has an input section 201, a facial-expression analyzing section 210, and a biometric-signal analyzing section 220.

The facial-expression analyzing section 210 has a low-frequency-component extracting section 211, an A/D converting section 212, a facial-expression-analysis-result generating section 213, and a facial-expression-analysis-information storage section 214.

On the other hand, the biometric-signal analyzing section 220 has a high-pass filter (high-frequency-component extracting section) 221, an amplifying section 222, an A/D converting section 223, a noise removing section 224, a biometric-signal-analysis-result generating section 225, and a biometric-signal-analysis-information storage section 226.

The input section 201 outputs a light-reception signal of the light-receiving section 103 to the facial-expression analyzing section 210 and the biometric-signal analyzing section 220 in parallel.

The output signal is a signal in which the following two types of reflection light are mixed.

(1) Skin-surface reflection light
(2) Subepidermal-tissue reflection light (diffuse light)

The facial-expression analyzing section 210 executes user-facial-expression analysis by executing a process of selecting and extracting "(1) skin-surface reflection light" from the signal in which the two types of signals are mixed and generates and outputs facial-expression analysis information 121 as a result of the analysis.

On the other hand, the biometric-signal analyzing section 220 executes user-bioinformation analysis by executing a process of selecting and extracting "(2) subepidermal-tissue reflection light (diffuse light)" from the signal in which the above-described two types of signals are mixed and generates and outputs the bioanalysis information 122 as a result of the analysis.

First, the processes executed by the facial-expression analyzing section 210 are explained.

The low-frequency-component extracting section 211 executes the process of selecting and extracting a low-frequency-component signal from the signal input from the input section 201.

The low-frequency-component extraction process executed by the low-frequency-component extracting section 211 is the process of selecting and extracting only the component "(1) skin-surface reflection light" from the mixed signal of the following two signal components, i.e., two optical signals which are (1) skin-surface reflection light, and
(2) subepidermal-tissue reflection light (diffuse light).

The two optical signals are included at the light-receiving section 103.

This process is explained with reference to FIGS. 5A, 5B, and 5C.

Figure 5:
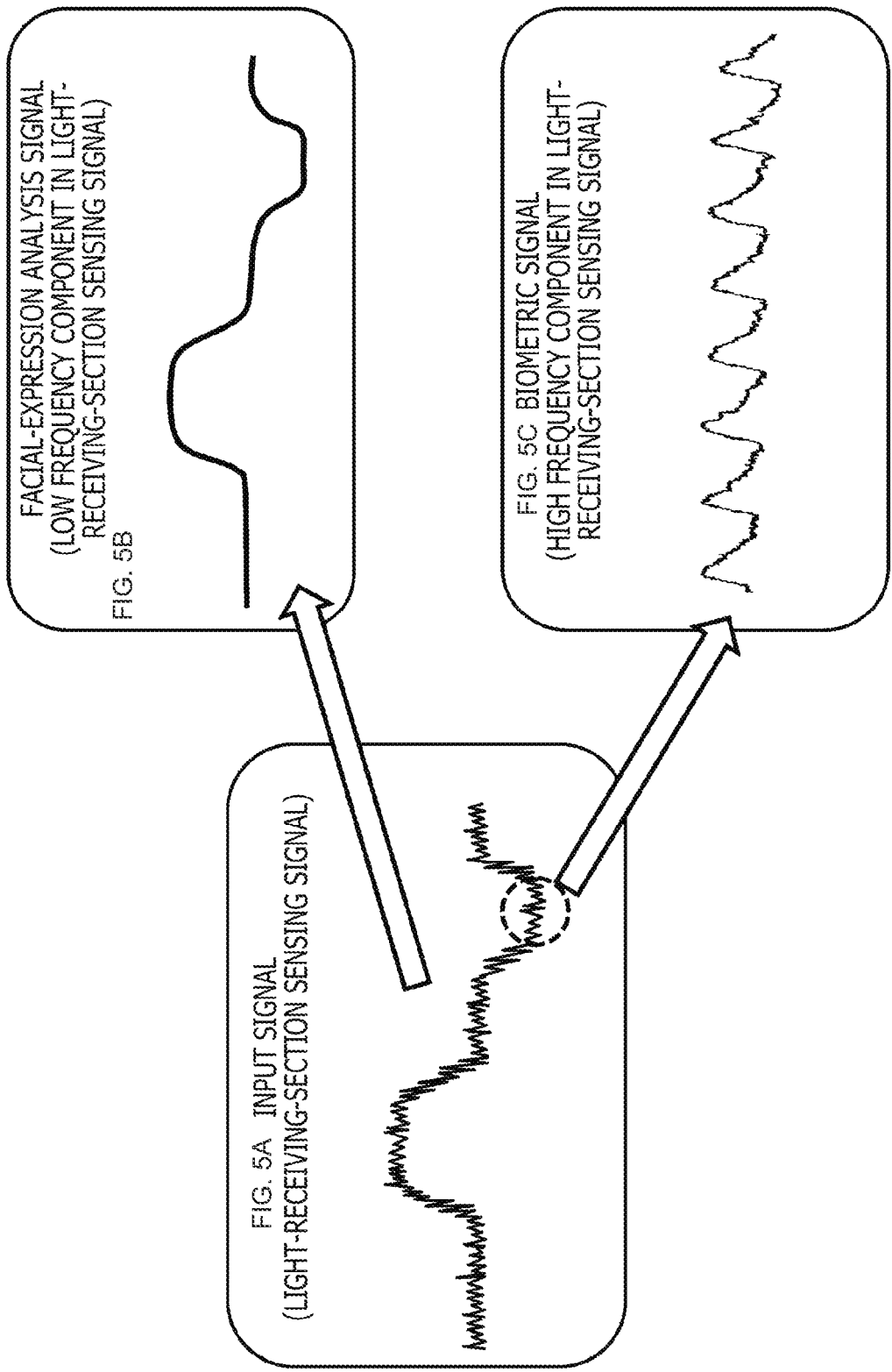
FIGS. 5A, 5B, and 5C are figures for explaining a process executed by the light-reception-signal analyzing section of the information processing apparatus of the present disclosure.

FIGS. 5A, 5B, and 5C depict the following three signals.

FIG. 5A Input signal (light-receiving-section sensing signal)

FIG. 5B Facial-expression analysis signal (low frequency component in the light-receiving-section sensing signal)

FIG. 5C Biometric signal (high frequency component in the light-receiving-section sensing signal)

The light-reception signal of the light-receiving section 103 is the signal depicted in FIG. 5A and is a mixed signal of a signal component with smaller temporal changes, i.e., a low frequency component, and a signal component with larger temporal changes, i.e., a high frequency component.

The low frequency component included in the light-reception signal of the light-receiving section 103 is equivalent to a signal component that accompanies a facial-expression change of the user (to-be-analyzed person) 10. That is, it is a signal reflecting facial-skin movements generated when the user laughs and so on.

On the other hand, the high frequency component included in the light-reception signal of the light-receiving section 103 is equivalent to a signal component reflecting periodic fluctuations generated by the blood flow through subepidermal blood vessels of the user (to-be-analyzed person) 10.

In such a manner, the low frequency component included in the light-reception signal of the light-receiving section 103 is a signal reflecting facial-skin movements and can be used for facial-expression analysis.

On the other hand, the high frequency component included in the light-reception signal of the light-receiving section 103 is a signal reflecting the state of blood flowing through blood vessels beneath the face and can be used for bioinformation analysis.

The low-frequency-component extracting section 211 of the facial-expression analyzing section 210 depicted in FIG. 4 extracts the low frequency component included in the light-reception signal of the light-receiving section 103. That is, the low-frequency-component extracting section 211 extracts reflection light for facial-expression analysis which is a signal reflecting facial-skin movements of the user (to-be-analyzed person) 10.

The facial-expression analysis signal (the low frequency component in the light-receiving-section sensing signal) extracted by the low-frequency-component extracting section 211 of the facial-expression analyzing section 210 depicted in FIG. 4 is input to the A/D converting section 212.

The A/D converting section 212 executes an A/D-conversion of the facial-expression analysis signal (the low frequency component in the light-receiving-section sensing signal) extracted by the low-frequency-component extracting section 211, converts the analog signal into a digital signal, and inputs the digital signal to the facial-expression-analysis-result generating section 213.

As mentioned before, the facial-expression analysis signal (low frequency component in the light-receiving-section sensing signal) extracted by the low-frequency-component extracting section 211 is a signal reflecting facial-skin movements of the user (to-be-analyzed person) 10.

Facial-skin movements differ corresponding to facial expressions of the face, i.e., facial expressions corresponding to laughter, anger, sorrow, and the like.

The facial-expression-analysis-information storage section 214 has stored thereon registration information regarding typical data patterns of facial-skin movements that correspond to various human facial expressions, i.e., facial expressions corresponding to laughter, anger, sorrow, and the like. Specifically, the facial-expression-analysis-information storage section 214 has stored thereon a learning model (facial-expression model) having corresponding data of facial-expression labels and feature data of skin-surface reflection-light signals reflecting skin-surface movements, the facial-expression labels corresponding to a plurality of different facial expressions.

Note that, as explained in detail in a latter section, reflection light acquired by the combinations of the light-emitting sections and the light-receiving sections includes a plurality of reflection-light signals obtained from different positions on the face of the user (to-be-analyzed person) 10, the different positions being, for example, a plurality of different positions such as the glabella, positions near the eyes, or the cheeks.

Information regarding skin movements that correspond to various facial expressions corresponding to various positions on a face are recorded on the facial-expression-analysis-information storage section 214.

Note that, by combining a plurality of pieces of bioinformation obtained from a plurality of different positions such as the glabella, positions near the eyes, or the cheeks, the precision of estimation of internal states such as affect can be enhanced. In addition, by using a plurality of sensors, it is also possible to remove noise at the time of body movements.

Information that is acquired corresponding to the positions of the sensors includes various kinds of information, and it is possible to perform a process of estimation of various different internal states that correspond to sensing information of the individual sensors.

Figure 6:
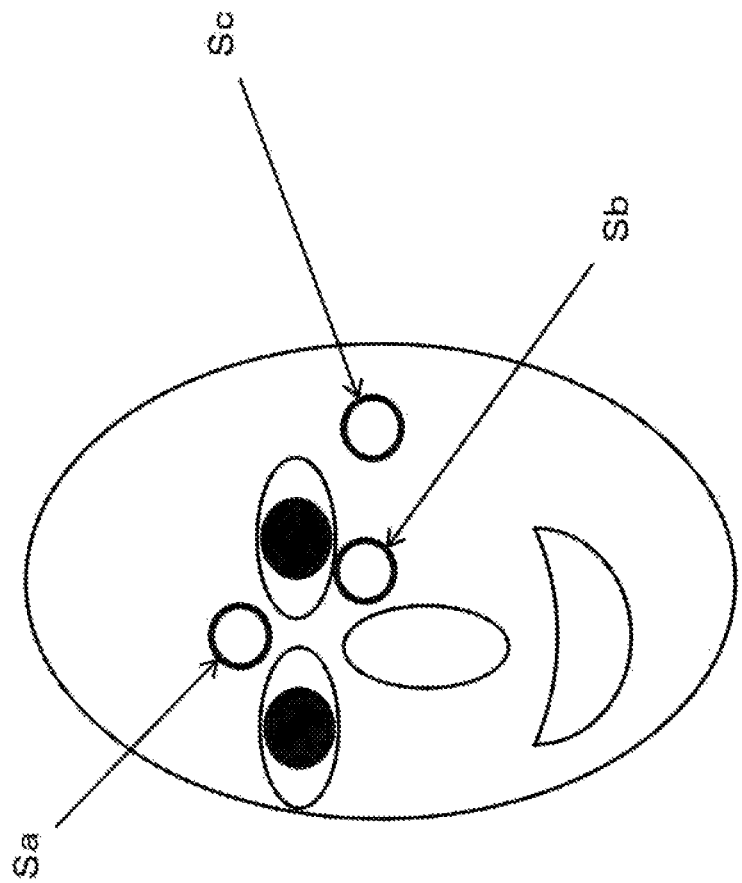
FIG. 6 is a figure for explaining an example of bioinformation measurement by using a plurality of sensors.

For example, as depicted in FIG. 6, because the blood flow rate of a forehead easily reflects affect, a sensor Sa near the glabella of the forehead is used to measure the blood flow rate, another sensor measures the pulse wave, and internal state estimation can be performed on the basis of information regarding the blood flow rate and pulse wave.

In addition, at the time of occurrence of a body movement, the pulse wave significantly reflects body movement noise undesirably, but body movement noise in the blood flow rate can be suppressed by introducing a body-movement suppression technology. Because of this, the information regarding the pulse wave can be complemented by using the information regarding the blood flow rate.

In addition, because, if the user blinks hard, a pulse wave sensed by a sensor Sb on the middle side of the face under the eyes depicted in FIG. 6 reflects body movement noise undesirably, a process of complementing the pulse wave sensed by a sensor Sc near a cheek on the lower outer side of an eye is possible.

The facial-expression-analysis-result generating section 213 compares and collates the facial-expression analysis signal (low frequency component in the light-receiving-section sensing signal) extracted by the low-frequency-component extracting section 211 and typical data patterns of facial-skin movements that correspond to various facial expressions, i.e., facial expressions corresponding to laughter, anger, sorrow, and the like, that are registered on the facial-expression-analysis-information storage section 214. Then, the facial-expression-analysis-result generating section 213 categorizes which of laughter, anger, sorrow, or the like the facial expression of the face of the user (to-be-analyzed person) 10 corresponds to. A result of the categorization is output as the facial-expression analysis information 121.

Next, processes executed by the biometric-signal analyzing section 220 of the light-reception-signal analyzing section 104 depicted in FIG. 4 are explained.

The high-pass filter (high-frequency-component extracting section) 221 executes a process of selecting and extracting a high frequency component, i.e., a high-frequency component signal, from a signal input from the input section 201.

The high-frequency-component extraction process executed by the high-pass filter (high-frequency-component extracting section) 221 is the process of selecting and extracting only the component "(2) subepidermal-tissue reflection light (diffuse light)" from the mixed signal of the following two signal components, i.e., two optical signals which are (1) skin-surface reflection light, and
(2) subepidermal-tissue reflection light (diffuse light).

The two optical signals are included at the light-receiving section 103.

As explained with reference to FIGS. 5A, 5B, and 5C earlier, the light-reception signal of the light-receiving section 103 is the signal depicted in FIG. 5A and is a mixed signal of a signal component with smaller temporal changes, i.e., a low frequency component equivalent to a low frequency component, and a signal component with larger temporal changes, i.e., a high frequency component.

The low frequency component included in the light-reception signal of the light-receiving section 103 is equivalent to a signal component that accompanies a facial-expression change of the user (to-be-analyzed person) 10. That is, the low frequency component is a signal reflecting facial-skin movements generated when the user laughs and so on.

On the other hand, the high frequency component included in the light-reception signal of the light-receiving section 103 is equivalent to a signal component reflecting periodic fluctuations generated by the blood flow through subepidermal blood vessels of the user (to-be-analyzed person) 10.

In such a manner, the high frequency component included in the light-reception signal of the light-receiving section 103 is a signal reflecting periodic fluctuations generated by the blood flow through the subepidermal blood vessels and can be used for bioinformation analysis.

The high-pass filter (high-frequency-component extracting section) 221 of a biometric-signal analyzing section 210 depicted in FIG. 4 extracts the high frequency component included in the light-reception signal of the light-receiving section 103. That is, the high-pass filter (high-frequency-component extracting section) 221 extracts reflection light for bioinformation analysis which is a signal reflecting the blood state such as a subepidermal blood flow of the user (to-be-analyzed person) 10.

The bioinformation analysis signal (high frequency component in the light-receiving-section sensing signal) extracted by the high-pass filter (high-frequency-component extracting section) 221 depicted in FIG. 4 is amplified at the amplifying section 222 and further input to the A/D converting section 223, to be converted into a digital signal.

The digital signal is subjected to a noise removal process at the noise removing section 224 and then input to the biometric-signal-analysis-result generating section 225.

As mentioned before, the bioinformation analysis signal (high frequency component in the light-receiving-section sensing signal) extracted by the high-pass filter (high-frequency-component extracting section) 221 is a signal reflecting the subepidermal blood state of the user (to-be-analyzed person) 10.

Specifically, information by which bioinformation such as a blood flow rate, a blood flow speed, a pulse wave, a blood pressure, a heart rate, a heart rate fluctuation, a blood oxygen concentration, or arterial oxygen saturation can be analyzed is included.

The biometric-signal-analysis-information storage section 226 has stored thereon various kinds of bioinformation of humans, i.e., feature data that corresponds to individual states of blood flow rates, blood flow speeds, pulse waves, blood pressures, heart rates, heart rate fluctuations, blood oxygen concentrations, and arterial oxygen saturation. Specifically, a learning model that has corresponding data of feature data of subepidermal reflection-light signals corresponding to a plurality of different biological states (blood flow rates, blood flow speeds, pulse waves, blood pressures, heart rates, heart rate fluctuations, blood oxygen concentrations, arterial oxygen saturation, etc.) is stored.

The biometric-signal-analysis-result generating section 225 compares and collates the bioinformation analysis signal (the high frequency component in the light-receivingsection sensing signal) extracted by the high-pass filter (high-frequency-component extracting section) 221 and the data registered on the biometric-signal-analysis-information storage section 226, i.e., data corresponding to each state such as a blood flow rate, a blood flow speed, a pulse wave, a blood pressure, a heart rate, a heart rate fluctuation, a blood oxygen concentration, or arterial oxygen saturation, and generates and outputs the bioanalysis information 122 of the user (to-be-analyzed person) 10.

[3. About Setting Example of Reflection-Light Measurement Points and Specific Configuration Example of Sensors]

Next, a setting example of reflection-light measurement points and a specific configuration example of sensors are explained.

Highly precisely analyzing facial expressions of a human face requires analyzing skin movements at different positions on the face.

As mentioned before, by analyzing skin movements at different positions on the face of the user (to-be-analyzed person) 10, for example, at a plurality of different positions such as the glabella, portions near the eyes, or the cheeks, it is possible to highly precisely analyze facial expressions of the user (to-be-analyzed person) 10 when he/she is laughing, sad, angry, and so on.

In order to realize highly precise analysis of facial expressions of a face, the information processing apparatus 100 of the present disclosure acquires light-reception signals reflecting skin movements at different positions on the face of the user (to-be-analyzed person) 10 and executes facial-expression analysis.

A setting example of measurement points is explained with reference to FIG. 7.

Figure 7:
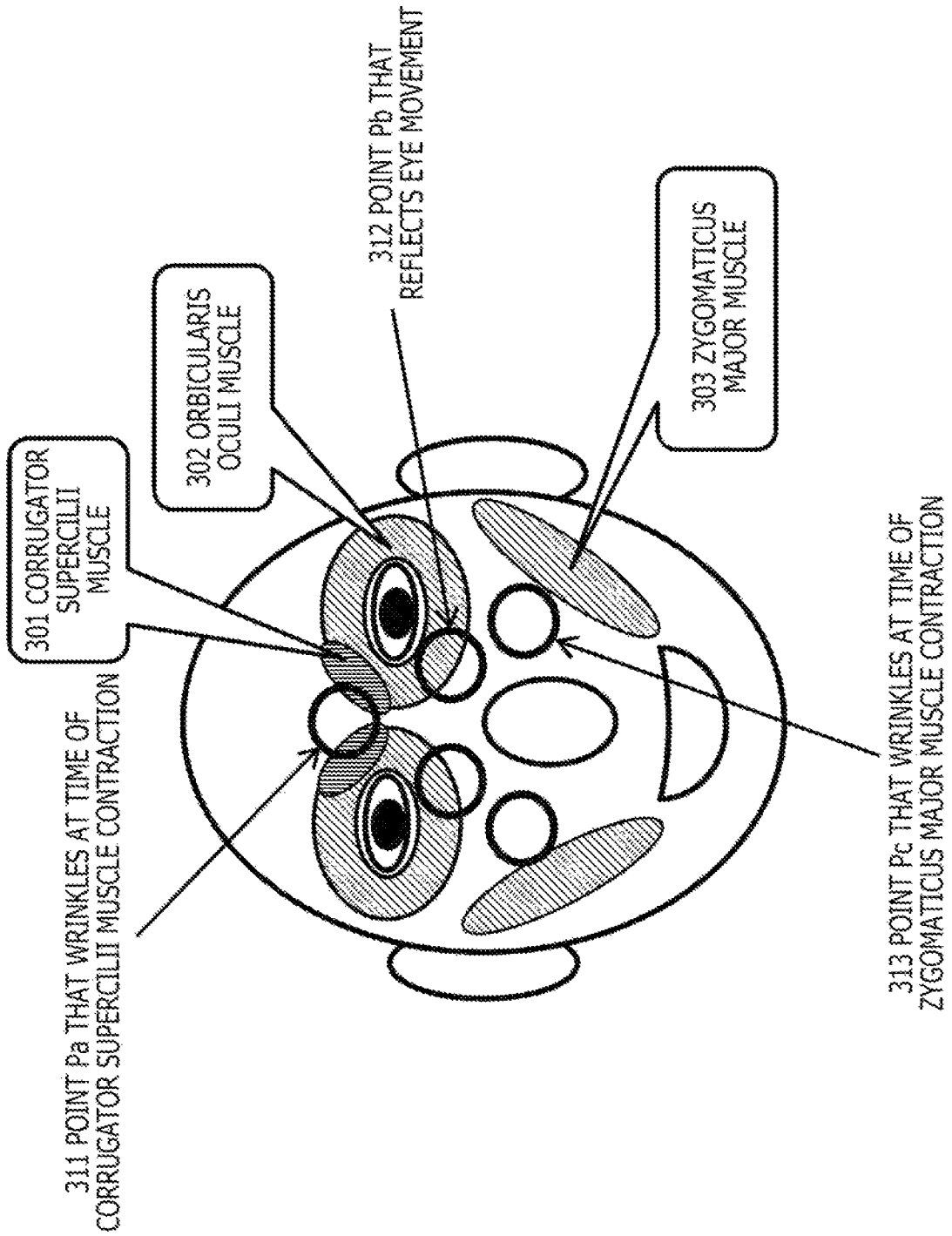
FIG. 7 is a figure for explaining a process executed by the information processing apparatus of the present disclosure.

An example depicted in FIG. 7 is a figure depicting one setting example of measurement points at which the information processing apparatus 100 of the present disclosure acquires reflection light.

As representative muscles that are included in a large number of muscles located beneath a face and exhibit significant changes corresponding to facial expressions, the following three muscles are depicted in FIG. 7.

Corrugator supercilii muscle 301
Orbicularis oculi muscle 302
Zygomaticus major muscle 303

These muscles generate large movements along with changes of facial expression of a face.

Further, there are points where the surface, i.e., the skin, of the face moves significantly corresponding to movements of those muscles. FIG. 7 depicts the following three points.

(a) Point Pa, 311 that wrinkles at the time of contraction of the Corrugator supercilii muscle 301
(b) Point Pb, 312 that moves significantly corresponding to movements of the Orbicularis oculi muscle 302, i.e., movements of an eye
(c) Point Pc, 313 that wrinkles at the time of contraction of the Zygomaticus major muscle 303

Note that there is one point Pb or Pc on each of the right and left sides.

By setting these points Pa, Pb, and Pc as reflection-light measurement points and analyzing reflection light at those points, user facial expressions (corresponding to laughter, anger, sorrow, etc.) can be analyzed highly precisely.

A specific configuration example for irradiating the skin at the plurality of measurement points with light and acquiring reflection light from the plurality of measurement points is explained with reference to FIGS. 8A and 8B.

FIG. 8A is a figure depicting a plurality of measurement points (five circles depicted in FIG. 8A) for highly precisely analyzing facial expressions of the face of a human that is explained with reference to FIG. 7.

FIG. 8B is a figure depicting a specific sensor setting example for irradiating positions on the skin that correspond to the five measurement points depicted in FIG. 8A with light and acquiring reflection light from those five measurement points.

FIG. 8B depicts the head-mounted display (HMD) 20 worn by the user.

An upper section of FIG. 8B depicts a figure in which the user has the HMD 20 on. A middle section depicts a surface of the HMD 20 to face the user, i.e., a surface on the side which abuts on the eyes of the user. Two middle white rectangular areas (L and R) in a figure depicted in the middle section of FIG. 8B are image display areas to be observed by the left eye and the right eye of the user, respectively.

A plurality of sensors, i.e., sensors including light emitting elements and light receiving elements, is provided on the user-worn surface of the HMD.

Five white circles depicted in the figure of the HMD user-worn surface in the middle section of FIG. 8B are sensors.

Each sensor has a configuration including a pair of a light emitting element 341 and a light receiving element 342 as depicted in a lower section of FIG. 8B.

The light emitting element 341 and the light receiving element 342 are equivalent to the light-emitting section 102 and the light-receiving section 103 of the information processing apparatus 100 depicted in FIG. 1.

Light output from the light emitting element 341 is reflected on the skin and subepidermal tissue (blood vessels, etc.) of the user, the reflection light is sensed by the light receiving element 342, and the sensed reflection-light signal is analyzed at the emission-light-signal analyzing section 104.

As depicted on the HMD user-worn surface in the middle section of FIG. 8B, the following five sensors are provided to the HMD.

Measurement sensor (Sa) 321 for a point that wrinkles at the time of corrugator supercilii muscle contraction
Left-eye-movement measurement sensor (SbL) 322L
Right-eye-movement measurement sensor (SbR) 322R
Measurement sensor (ScL) 323L for a point that wrinkles at the time of left zygomaticus major muscle contraction
Measurement sensor (ScR) 323R for a point that wrinkles at the time of right zygomaticus major muscle contraction These five sensors are ones that are provided in association with skin positions that exhibit large movements corresponding to human facial expressions (facial expressions corresponding to laughter, anger, sorrow, and the like) as explained with reference to FIG. 7 earlier.

By analyzing skin reflection light of those plurality of sensors, human facial expressions can be analyzed highly precisely.

Note that feature data of reflection light that accompanies facial-expression changes at those five points is acquired by a learning process or the like executed in advance and is stored on the facial-expression-analysis-information storage section 214 in advance.

The facial-expression-analysis-result generating section 213 depicted in FIG. 4 compares and collates five signals (skin reflection-light signals) acquired by the five sensors of the HMD worn by the user who is a person to be subjected to measurement and typical data patterns of facial-skin movements that correspond to various facial expressions, i.e., facial expressions corresponding to laughter, anger, sorrow, and the like, that are registered on the facial-expression-analysis-information storage section 214. Then, the facial-expression-analysis-result generating section 213 categorizes which of laughter, anger, sorrow, or the like the facial expression of the face of the user (to-be-analyzed person) 10 corresponds to. A result of the categorization is output as the facial-expression analysis information 121.

Figure 9:
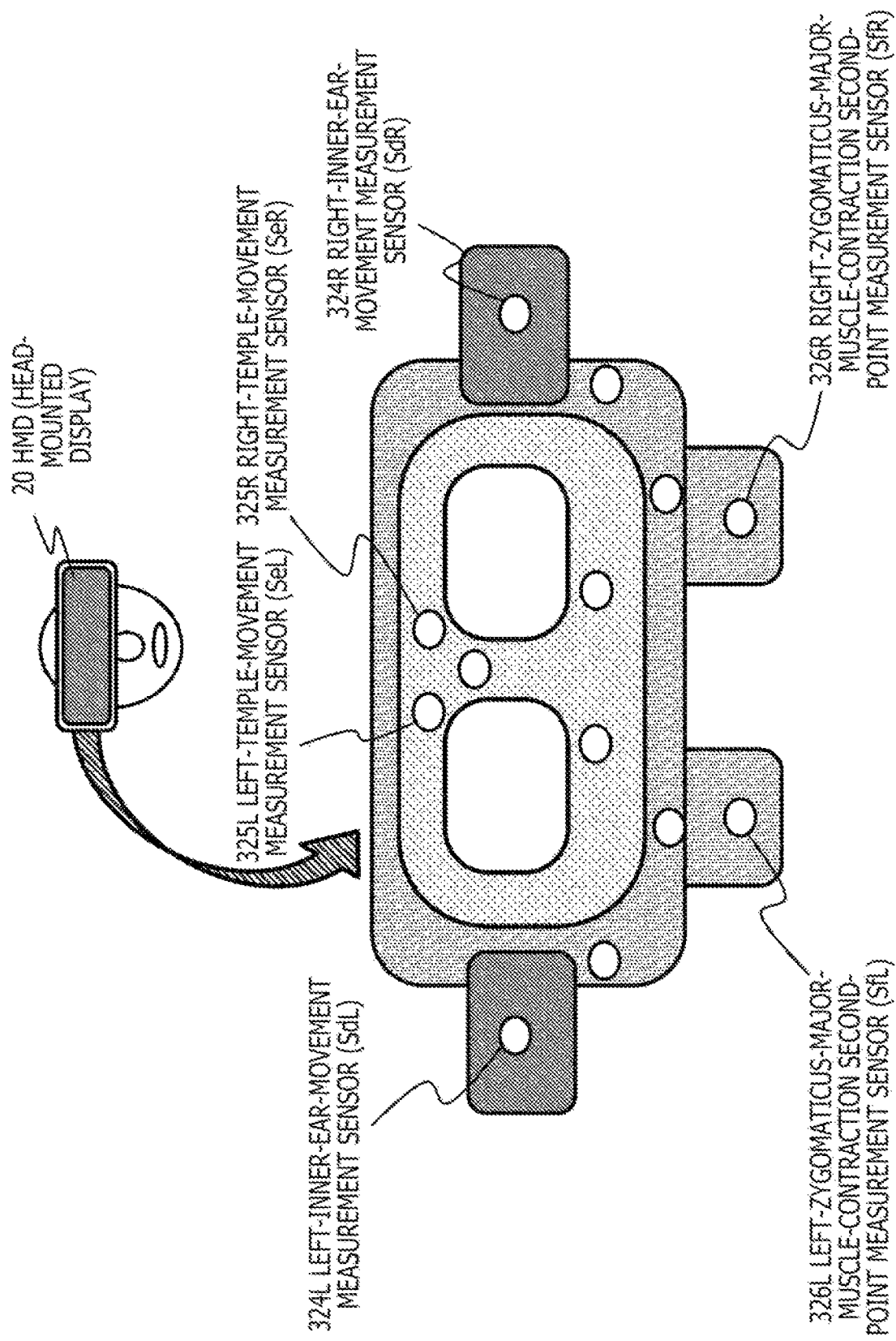
FIG. 9 is a figure for explaining a sensor configuration example of the information processing apparatus of the present disclosure.

Note that the attachment positions of the sensors depicted in FIGS. 8A and 8B are examples, and, in another possible configuration, more sensors may be provided. For example, in an example depicted in FIG. 9, an HMD has the following sensors in addition to the five sensors depicted in FIGS. 8A and 8B.

Left-inner-ear-movement measurement sensor (SdL) 324L

Right-inner-ear-movement measurement sensor (SdL) 324R

Left-temple-movement measurement sensor (SeL) 325L

Right-temple-movement measurement sensor (SeR) 325R

Measurement sensor (SfL) 326L for a second point that wrinkles at the time of left zygomaticus major muscle contraction Measurement sensor (SfR) 326R for a second point that wrinkles at the time of right zygomaticus major muscle contraction In addition, while a configuration example using an HMD is explained here, the present disclosure can be applied not only to HMDs, but also to a configuration using general wearable equipment (headphones, earphones, etc.) to be worn on a face.

For example, change data about reflection light at these points is also acquired by a learning process in advance, and stored on the facial-expression-analysis-information storage section 214 in advance.

The facial-expression-analysis-result generating section 213 depicted in FIG. 4 compares and collates a signal (skin reflection-light signal) acquired by each sensor of the HMD worn by the user who is a person to be subjected to measurement and feature data of facial-skin movements, i.e., typical data patterns, of various facial expressions, i.e., facial expressions corresponding to laughter, anger, sorrow, and the like, that are registered on the facial-expression-analysis-information storage section 214. Then, the facial-expression-analysis-result generating section 213 categorizes which of laughter, anger, sorrow, or the like the facial expression of the face of the user (to-be-analyzed person) 10 corresponds to. A result of the categorization is output as the facial-expression analysis information 121.

By providing many sensor positions in such a manner, more highly precise facial-expression analysis becomes possible.

Note that, while it is made possible to execute a facial-expression analysis process and a bioanalysis process together on the basis of sensing information of one sensor in the configuration of the present disclosure, configurations like the ones below may further be adopted. For example, in another possible configuration, an infrared laser may be used as a light source, and a sensor that measures a blood flow rate and a blood flow speed together with facial-expression information may be used. Specifically, for example, in one possible configuration, a dual-wavelength LED may be used as a light source, and thereby a sensor that measures arterial oxygen saturation together with facial-expression information may be used.

[4. About Configuration and Processes for Realizing Highly Precise Facial-Expression Analysis Process]

Next, a configuration and processes for highly precisely executing facial-expression analysis of the user (to-be-analyzed person) 10 in the information processing apparatus 100 of the present disclosure are explained.

As explained earlier, the facial-expression-analysis-result generating section 213 depicted in FIG. 4 compares and collates signals (skin reflection-light signals) acquired by the sensors of the HMD worn by the user who is a person to be subjected to measurement and typical data patterns of facial-skin movements that correspond to various facial expressions, i.e., facial expressions corresponding to laughter, anger, sorrow, and the like, that are registered on the facial-expression-analysis-information storage section 214, and categorizes which of laughter, anger, sorrow, or the like the facial expression of the face of the user (to-be-analyzed person) 10 corresponds to. A result of the categorization is output as the facial-expression analysis information 121.

The facial-expression-analysis-information storage section 214 has stored thereon feature data of reflection light that accompanies facial-expression changes, i.e., a learning model. The data of the facial-expression-analysis-information storage section 214 is model data that is acquired by a learning process or the like executed in advance and that is stored on the facial-expression-analysis-information storage section 214. Specifically, the facial-expression-analysis-information storage section 214 stores a learning model (facial-expression model) having corresponding data of facial-expression labels and feature data of skin-surface reflection-light signals reflecting skin-surface movements, the facial-expression labels corresponding to a plurality of different facial expressions.

Hereinafter, an example of the learning process is explained.

Figure 10:
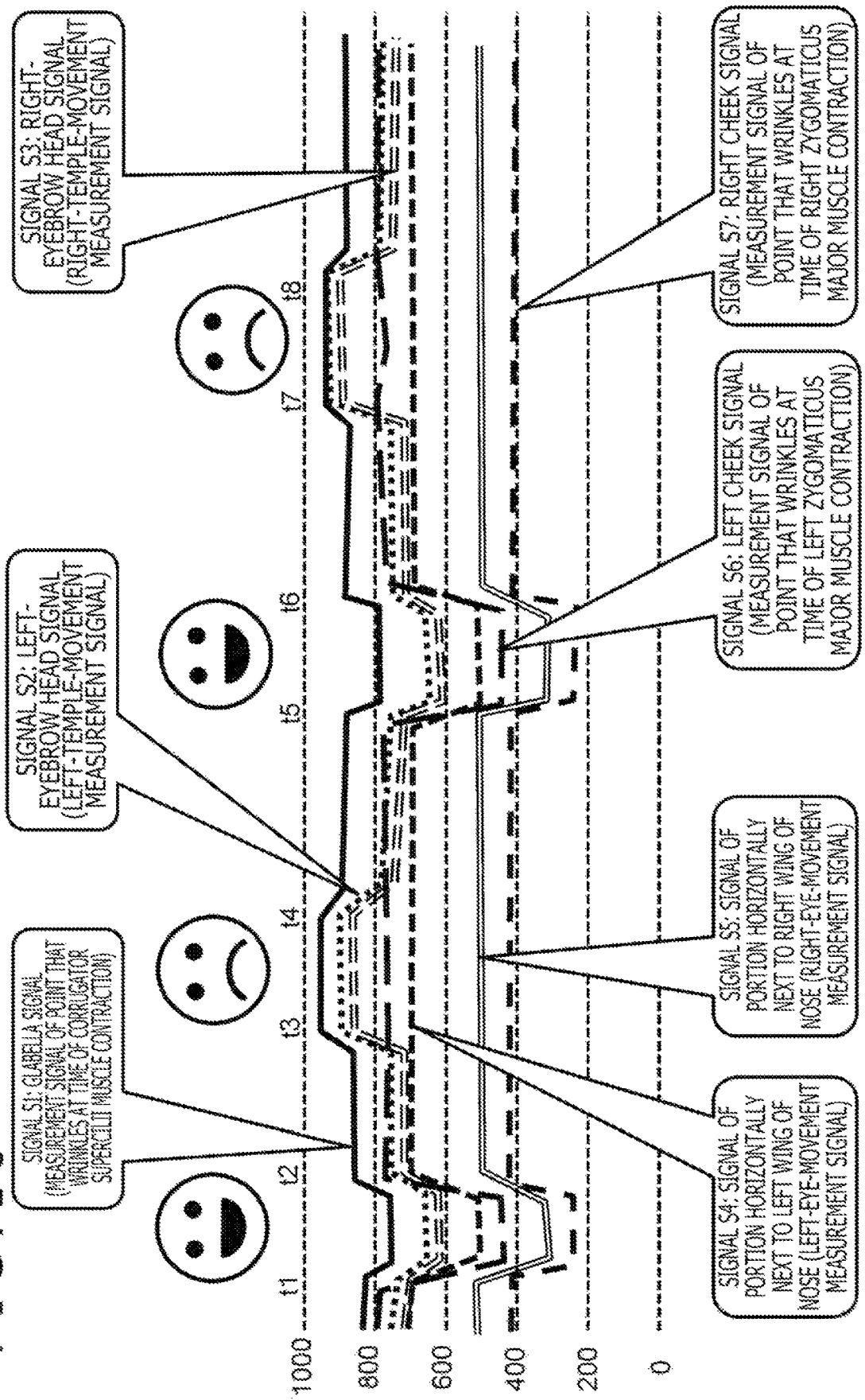
FIG. 10 is a figure for explaining a process executed by the light-reception-signal analyzing section of the information processing apparatus of the present disclosure.

FIG. 10 depicts an example of signals acquired for generating the learning model to be stored on the facial-expression-analysis-information storage section 214.

Data depicted in FIG. 10 is data representing, along the time axis, input signals from sensors attached to respective positions on the HMD.

Time elapses from left to right.

FIG. 10 depicts time-series data of the following seven signals S1 to S7.

Signal S1: glabella signal (measurement signal of a point that wrinkles at the time of corrugator supercilii muscle contraction)

Signal S2: left-eyebrow head signal (left-temple-movement measurement signal)

Signal S3: right-eyebrow head signal (right-temple-movement measurement signal)

Signal S4: signal of a portion horizontally next to the left wing of a nose (left-eye-movement measurement signal)

Signal S5: signal of a portion horizontally next to the right wing of a nose (right-eye-movement measurement signal)

Signal S6: left cheek signal (measurement signal of a point that wrinkles at the time of left zygomaticus major muscle contraction)

Signal S7: right cheek signal (measurement signal of a point that wrinkles at the time of right zygomaticus major muscle contraction)

Each of these signals exhibits a change corresponding to a facial expression (corresponding to laughter, anger, sorrow, etc.) of the face of the user (to-be-analyzed person) 10.

For example, the following facial expressions are observed.

A laughing face during the time t1 to t2
An angry face during the time t3 to t4
A laughing face during the time t5 to t6
An angry face during the time t7 to t8

The signals S1 to S7 exhibit similar signal changes in the periods of the laughing faces during the time t1 to t2 and the time t5 to t6, for example.

In addition, for example, the signals S1 to S7 exhibit similar signal changes in the periods of the angry faces during the time t3 to t4 and the time t7 to t8.

It becomes possible to analyze user facial expressions from features of signal changes in such a manner.

For this purpose, it becomes necessary to construct a learning model having the feature data.

A process of generating the learning model is explained.

First, data like the one depicted in FIG. 10 is acquired, and a normalization process (Nornalization) on the acquired data is executed. A data example after the normalization is depicted in FIG. 11.

The normalization process is executed as a process of setting, to a baseline, each signal (S1 to S7) that is observed when the user gives a serious look (e.g., output 0).

For example, it is sufficient to execute a calibration in which the user wearing the HMD is asked to give a serious look and an output value acquired from each sensor at that time is set to a baseline (e.g., output 0).

Note that, in order to suppress fluctuations of baselines attributable to misalignment of the attachment of the HMD and the like, a process in which it is deemed that a facial expression is a serious look if there are no fluctuations of sensor signals for a certain length of time and sensing values at this time are set to baselines (e.g., output 0) may be performed.

An example of a process of generating a learning model based on the normalized data is explained with reference to FIG. 12 and the subsequent figures.

As a technique of a machine learning process for constructing a learning model, a hidden Markov model can be used, for example.

It is also possible to construct a learning model as a model corresponding to each individual, and it is also possible to generate a model as a general-purpose model not intended for a particular user. Note that, in a case where a general-purpose model is constructed, a model construction is preferably performed by acquiring a large number of pieces of sample data to be applied to learning.

For example, the learning model is generated as a model in which a label of each user facial expression, that is, for example, each facial expression such as a serious look, a smile, an angry face, or a sad face, is associated with signal features.

Time-series signals depicted in FIG. 12 are signals similar to the normalized signals of the signals in FIG. 10, i.e., signals similar to the signals depicted in FIG. 11.

A smile during the time t1 to t2
An angry face during the time t3 to t4
A smile during the time t5 to t6
An angry face during the time t7 to t8

Note that sensing signals of the sensors exhibit significant changes during the time when a serious look turns into a smile and during the time when a serious look turns into an angry face. Similarly, sensing signals of the sensors exhibit significant also changes during the time when a smile returns to a serious look and during the time when an angry face returns to a serious look.

The time when a serious look turns into a smile and the time and period when a serious look turns into an angry face are called onset time and an onset period.

On the other hand, the time when a smile returns to a serious look and the time and period when an angry face returns to a serious look are called offset time and an offset period.

As depicted in a lower section of FIG. 12, there are necessarily onset periods and offset periods when changes of facial expressions of a smile, a serious look, and an angry face occur.

By analyzing feature data of signal changes of those onset periods and offset periods, it becomes possible to more surely analyze changes of user facial expressions.

FIGS. 13A and 13B are figures depicting execution sequences of a learning-model construction process by a learning process and a facial-expression analysis process by using the constructed learning model.

FIG. 13A AT TIME OF LEARNING is a figure depicting the sequence of the learning-model construction process by a learning process.

FIG. 13B AT TIME OF EXECUTION OF FACIAL-EXPRESSION ANALYSIS PROCESS is a figure depicting the execution sequence of the facial-expression analysis process by using the constructed learning model.

First, FIG. 13A at the time of learning, the following data is input as input data.

(1) Light-receiving-section-output time-series data (multi-channel: S1, S2, . . . )
(2) Facial-expression labels (1: serious look, 2: smile, 3: angry face, . . . )

"(1) Light-receiving-section-output time-series data (multi-channel: S1, S2, . . . )" is time-series data of output signals from the sensors attached to the HMD. That is, it is data such as the signals S1 to S7 explained with reference to FIG. 10 earlier.

"(2) Facial-expression labels (1: serious look, 2: smile, 3: angry face, . . . )" are each a label of one facial expression defined in advance. In the learning model, feature data corresponding to the labels is associated.

The input data, i.e., the following data, is input to a learner 401.

(1) Light-receiving-section-output time-series data (multi-channel: S1, S2, . . . )
(2) Facial-expression labels (1: serious look, 2: smile, 3: angry face, . . . )

The learner 401 executes a learning process based on the input data. That is, the learner 401 executes a process of associating feature data of a signal with each label.

By this learning process, a facial-expression model depicted as an output of FIG. 13A AT TIME OF LEARNING in FIGS. 13A and 13B, i.e., a facial-expression model which is a learning model, is generated and is stored on the facial-expression-analysis-information storage section 214.

The facial-expression-analysis-information storage section 214 stores the learning model (facial-expression model) in which feature data corresponding to the facial-expression labels (1: serious look, 2: smile, 3: angry face, . . . ) is associated.

Note that the feature data of the model also includes signal change data of onset and offset timings explained with reference to FIG. 12 earlier.

FIG. 13B AT TIME OF EXECUTION OF FACIAL-EXPRESSION ANALYSIS PROCESS depicted in FIGS. 13A and 13B are figures depicting the execution sequence of the facial-expression analysis process by using the constructed learning model.

Input data FIG. 13B at the time of execution of the facial-expression analysis process is
(1) light-receiving-section-output time-series data (multi-channel: S1, S2, . . . ).

The input data is input to the light-reception-signal analyzing section 104.

The facial-expression analyzing section 210 of the light-reception-signal analyzing section 104 explained with reference to FIG. 4 refers to the learning model recorded on the facial-expression-analysis-information storage section 214, i.e., the learning model (facial-expression model) in which the feature data corresponding to the facial-expression labels (1: serious look, 2: smile, 3: angry face, . . . ) is associated, selects feature data that is determined as being the most similar to the input signal, and selects and outputs a facial-expression label (1: serious look, 2: smile, 3: angry face, . . . ) associated with the feature data.

Output data FIG. 13B at the time of execution of the facial-expression analysis process is
(1) facial-expression labels (1: serious look, 2: smile, 3: angry face, . . . ).

In such a manner, at the time of execution of a facial-expression analysis process, user-facial-expression analysis is executed by using the learning model generated in advance, i.e., the learning model (facial-expression model) in which the feature data corresponding to the facial-expression labels (1: serious look, 2: smile, 3: angry face, . . . ) is associated.

FIG. 14 is a figure for explaining a specific example of a learning-model generation process.

FIG. 14 depicts an example of a learning-model generation process by using a hidden Markov model (HMM).

The process is executed by procedures of (Step S01) and (Step S02) depicted in FIG. 14.

A process of each step is explained.

(Step S01)

First, at Step S01, an onset period is set by automatic or manual sectioning, and a label is given to the onset period.

For example, a user to be the target of learning model generation is given an instruction from a system (the information processing apparatus) or an operator by being told, "show me a smile now."

The system (information processing apparatus) analyzes sensor sensing values that accompany user-facial-expression changes corresponding to the instruction.

The example depicted in the figure is an example of analyzing sensor acquisition values in a process during which a serious look of the user turns into a smile, i.e., an onset period.

The example depicted in the figure is an example of analyzing time-series data of sensing values of sensors attached to three different positions on the user face.

For example, changes of signals are analyzed for each unit period (e.g., 0.2 seconds) that is defined in advance. Specifically, when the variance in the period that is defined in advance (e.g., 0.2 seconds) exceeds a threshold that is defined in advance, it is deemed that there is a facial-expression change from a serious look to a smile, and the period is set as an onset period by sectioning.

(Step S02)

The process of Step S01 is executed repeatedly to acquire a plurality of pieces of data, and common feature data obtained from the plurality of pieces of data, the common feature data being, for example, the average value or the like, is acquired and recorded as feature data corresponding to smiles.

Note that, as mentioned before, in one possible configuration, the learning model may be constructed as a learning model corresponding to an individual, or it is also possible to construct the learning model as a general-purpose learning model that can be applied to various users on the basis of data obtained from a plurality of subjects.

In a case where a learning model corresponding to an individual is to be generated, data collected at Step S02 is data of the particular individual.

On the other hand, in a case where a general-purpose learning model is to be generated, data collected at Step S02 is data obtained from various different subjects.

For example, in a case where a large number of pieces of data from a large number of subjects, i.e., large-scale data, can be collected, a general-purpose learning model can be constructed by applying machine learning based on a DNN (Deap Neural Network) which is a multilayer neural network.

FIG. 15 is a figure for explaining a specific example of a facial-expression analysis process by using a learning model (hidden Markov model) generated according to the process depicted in FIG. 14.

As depicted in (PROCESS) in FIG. 15, the information processing apparatus that executes user-facial-expression analysis first acquires acquisition signals of sensors that sense reflection light of the facial skin of the user.

Further, data in a period that is estimated as being an onset period is retrieved on the basis of analysis data, that is, for example, the variance or the like, corresponding to the acquisition signals.

Further, the likelihood of the retrieved data and feature data corresponding to each facial-expression label in the learning model (facial-expression model) is computed.

Last, a facial-expression label set corresponding to feature data with high likelihood (with a high similarity) is determined as a user facial expression.

Analysis of user facial expressions is executed by these processes.

Note that, while only the type (a smile) of a user facial expression is categorized in the facial-expression analysis process explained with reference to FIG. 15, it is also possible to compute the intensity of a user facial expression by generating a learning model for analyzing the intensity of a facial expression such as the intensity of a smile, i.e., an intense smile or a light smile, and applying the learning model.

An example of a process of computing the intensity of a facial expression is explained with reference to FIG. 16.

Figure 16:
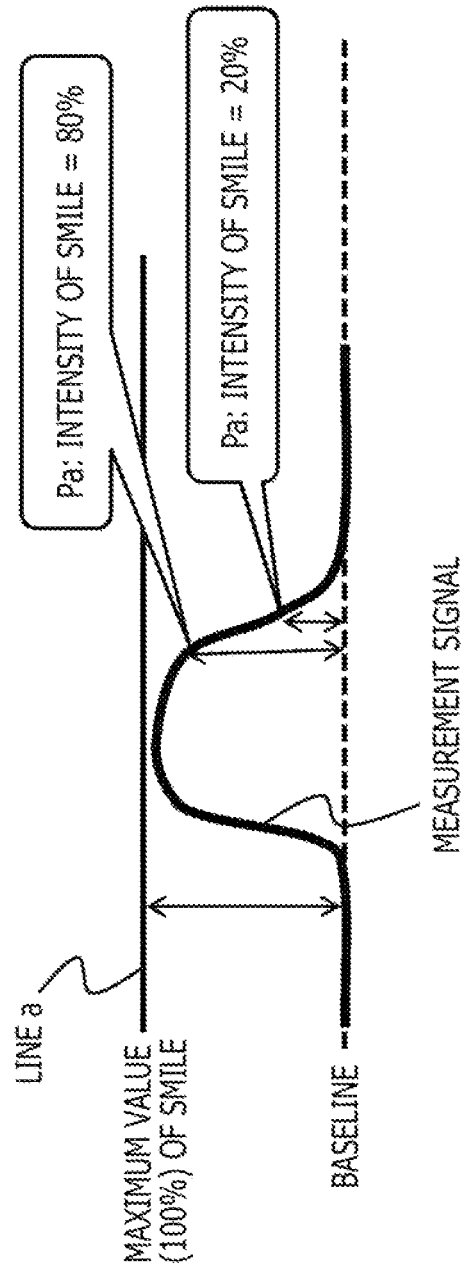
FIG. 16 is a figure for explaining a learning process and an analysis process executed by the information processing apparatus of the present disclosure.

The example depicted in FIG. 16 is an example of a process of estimating the intensity of a smile. A signal value (line a) whose degree of deviation from a baseline (at the time of a serious look) is the largest of signal values obtained from the user at the time of a learning process is recorded in the learning model as the maximum value of smiles (the degree of smile=100%).

By computing the ratio of data (a measurement signal) obtained at the time of user facial-expression analysis to the line a representing the maximum value of smiles (the degree of smile=100%), the intensity of a smile of the user can be computed.

It can be estimated that the intensity of smile=80% at the point pa depicted in the figure and that the intensity of smile=20% at the point pb depicted in the figure.

Note that, while only smile analysis is explained with reference to FIG. 14 to FIG. 16, processes about an angry face, a sad face, and the like are different only in terms of feature data, and similar process procedures are performed therefor.

[5. About Specific Example of Bioinformation Analysis Process]

Next, a specific example of a bioinformation analysis process executed by the biometric-signal analyzing section 220 of the light-reception-signal analyzing section 104 depicted in FIG. 4 is explained.

As explained with reference to FIG. 4 earlier, the biometric-signal analyzing section 220 of the light-reception-signal analyzing section 104 depicted in FIG. 4 executes user-bioinformation analysis by selecting and extracting the subepidermal-tissue reflection light (diffuse light) from the light-reception signal of the light-receiving section 103 and generates and outputs the bioanalysis information 122 as a result of the analysis.

The high frequency component included in the light-reception signal of the light-receiving section 103 is a signal reflecting periodic fluctuations generated by the blood flow through the subepidermal blood vessels and can be used for bioinformation analysis.

The biometric-signal analyzing section 220 analyzes the high frequency component included in the light-reception signal of the light-receiving section 103 and analyzes bioinformation such as a blood flow rate, a blood flow speed, a pulse wave, a blood pressure, a heart rate, a heart rate fluctuation, a blood oxygen concentration, or arterial oxygen saturation.

Figure 17:
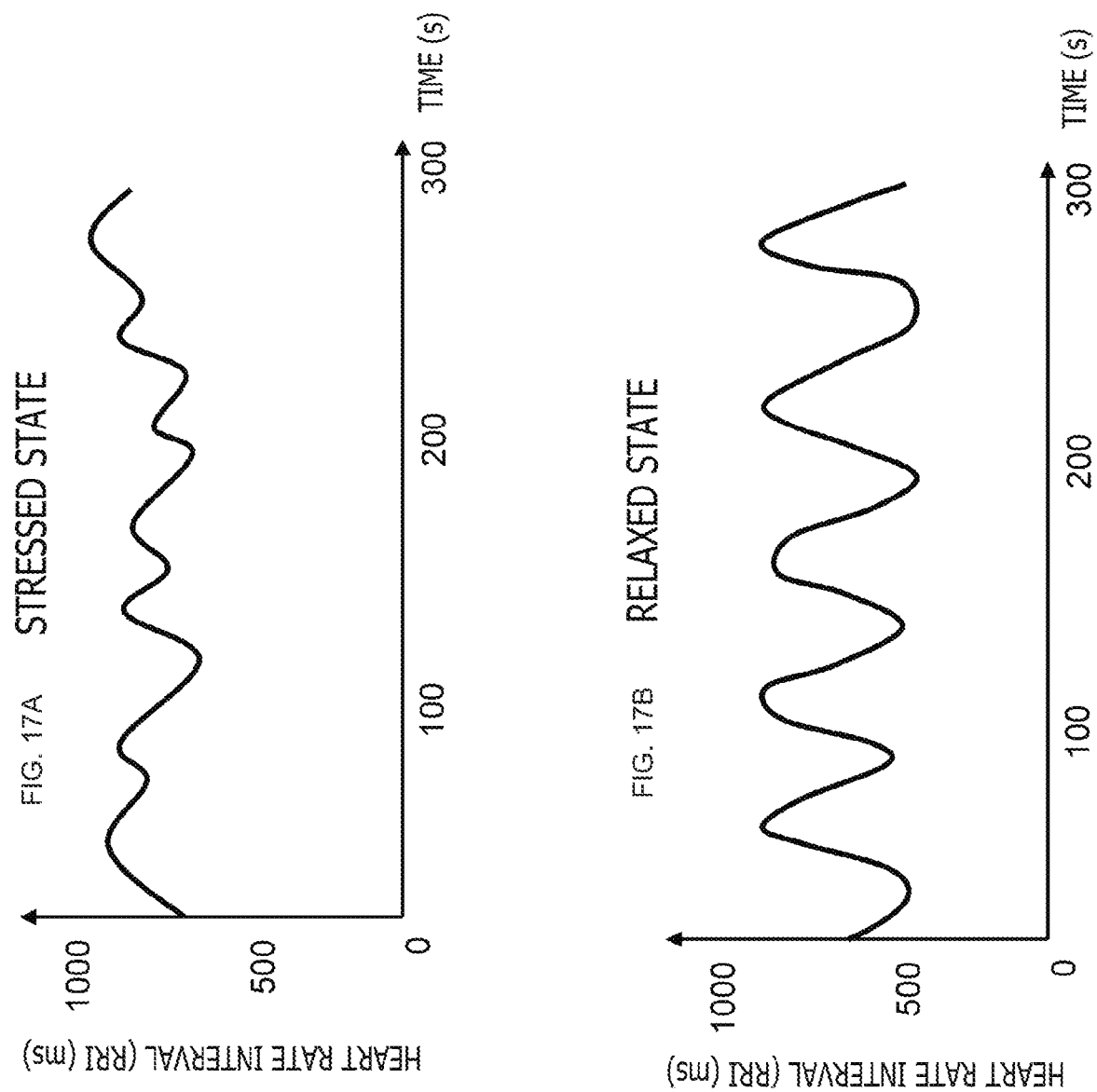
FIGS. 17A and 17B are figures for explaining an example of a biometric-signal analysis process executed by the information processing apparatus of the present disclosure.

FIGS. 17A and 17B depict temporal transition data of heart rate interval (RRI (ms)) in the following two user states.

FIG. 17A Stressed state
FIG. 17B Relaxed state

As depicted in the figure, changes that are observed along with the temporal transition of the heart rate interval of the user corresponding to each state have obviously different features.

It becomes possible to estimate the state of the user by recording the feature data corresponding to each state as learning data and by performing an analysis process by using the learning data.

In such a manner, bioinformation such as a blood flow rate, a pulse wave, or oxygen saturation is influenced by the autonomous nerve activity. That is, bioinformation exhibits changes corresponding to the internal state of the user such as a tense state, an excited state, or a stressed state.

Accordingly, it is possible to determine the internal state of the user, i.e., whether the user is feeling stressed or is relaxed, by observing fluctuations of the heart rate interval of the user, for example.

Figure 18:
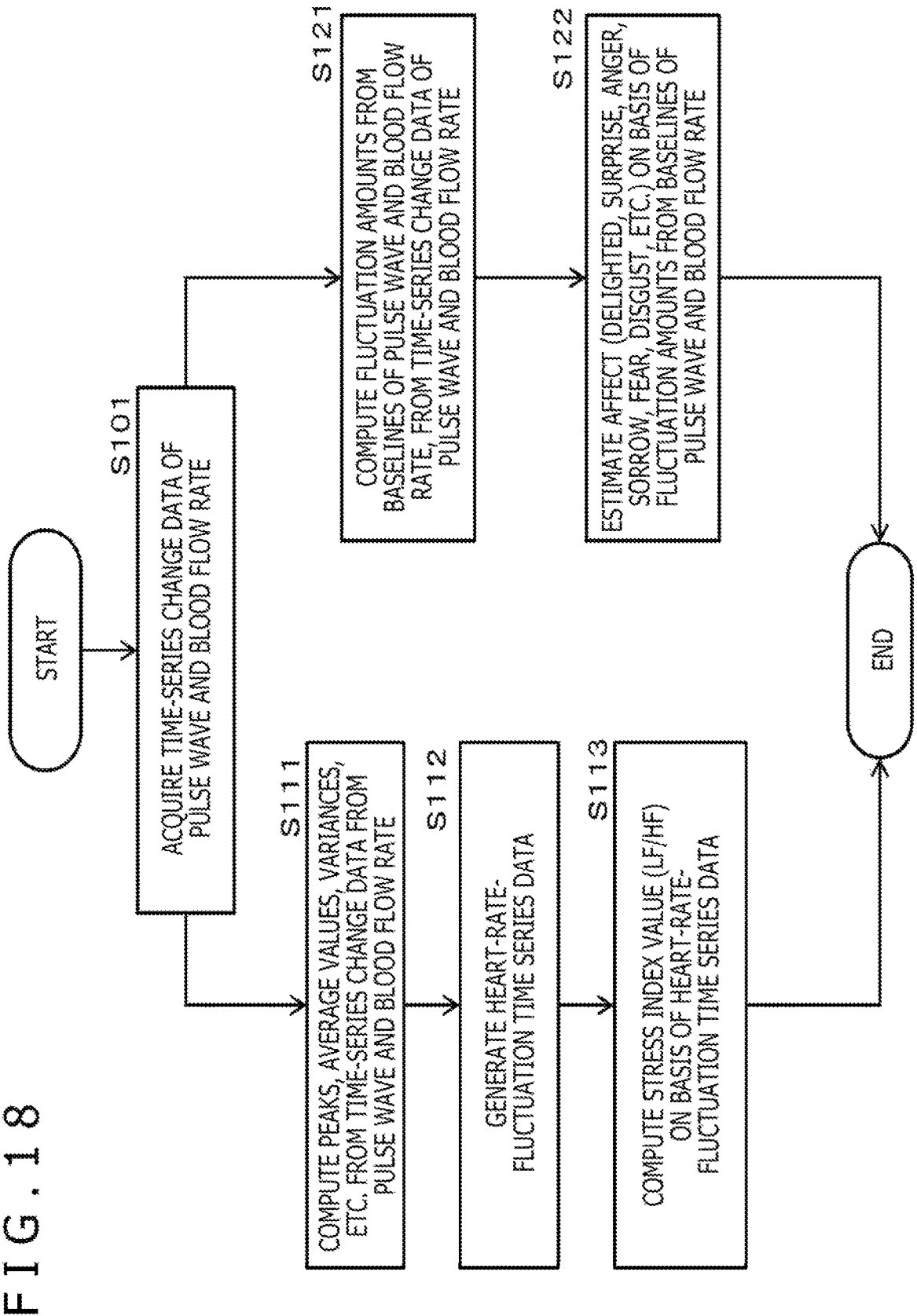
FIG. 18 is a figure depicting a flowchart for explaining a sequence of the biometric-signal analysis process executed by the information processing apparatus of the present disclosure.

A flowchart depicted in FIG. 18 is a flowchart for explaining one process sequence example of a bioinformation analysis process executed by the biometric-signal analyzing section 220 of the light-reception-signal analyzing section 104 depicted in FIG. 4.

Note that the process according to the flowchart depicted in FIG. 18 and the subsequent figures can be executed according to a program stored on the storage section of the information processing apparatus 100. For example, the process can be performed as a program execution process performed by a processor such as a CPU having a program execution functionality.

Hereinafter, a process of each step in the flow is explained sequentially.

Note that the flow depicted in FIG. 18 is a sequence of processes executed by the biometric-signal-analysis-result generating section 225 in the biometric-signal analyzing section 220 of the light-reception-signal analyzing section 104 depicted in FIG. 4.

(Step S101)

First, the biometric-signal-analysis-result generating section 225 of the biometric-signal analyzing section 220 acquires time-series data such as a pulse wave or a blood flow rate by an analysis process on a high frequency component included in a light-reception signal of the light-receiving section 103.

As explained with reference to FIG. 4 earlier, the biometric-signal-analysis-result generating section 225 compares and collates the bioinformation analysis signal (the high frequency component in the light-receiving-section sensing signal) extracted by the high-pass filter (high-frequency-component extracting section) 221 and the data registered on the biometric-signal-analysis-information storage section 226, i.e., data corresponding to each state such as a blood flow rate, a blood flow speed, a pulse wave, a blood pressure, a heart rate, a heart rate fluctuation, a blood oxygen concentration, or arterial oxygen saturation. Then, the biometric-signal-analysis-result generating section 225 generates bioinformation, such as time-series data such as a pulse wave or a blood flow rate, of the user (to-be-analyzed person) 10.

(Steps S111 to S113)

Processes at next Steps S111 to S113 and processes at Steps S121 to S122 are processes executed selectively or in parallel at the biometric-signal-analysis-result generating section 225.

First, the processes at Steps S111 to S113 are explained.

At Step S111, peaks, the average value, the variance, and the like are computed from the time-series change data of the pulse wave and the blood flow rate.

Next, at Step S112, heart-rate-fluctuation time series data is generated from the data acquired at Step S111. The heart-rate-fluctuation time series data is the data depicted in FIGS. 17A and 17B, for example.

Last, at Step S113, a stress index value (LH/HF (=(Low Frequency)/(High Frequency)) is computed on the basis of the heart-rate-fluctuation time series data and is output as the bioanalysis information 122.

The stress index value (LH/HF) is a stress index value computed on the basis of the heart-rate-fluctuation time series data. (LH/HF) is the palance value of the sympathetic nerve (LF) and the parasympathetic nerve (HF), and the degree of stress of the user is determined on the basis of the balance value.

Note that the process of computing the stress index value (LH/HF) itself based on the heart-rate-fluctuation time series data is a conventionally-known existing technology.

(Steps S121 and S122)

Next, the processes at Steps S121 and S122 are explained.

At Step S122, fluctuation amounts from pulse-wave and blood-flow-rate baselines are computed from the time-series change data of the pulse wave and the blood flow rate.

Note that the baselines in this case are equivalent to state values of the pulse waves and the blood flow rate at the time of the normal state.

Next, at Step S122, the affect of the user (delighted, surprise, anger, sorrow, fear, disgust, etc.) is estimated on the basis of the fluctuation amounts from the pulse-wave and blood-flow-rate baselines and is output as the bioanalysis information 122.

Note that the affect estimation process is executed by applying a learning model generated by a learning process executed in advance. Specifically, the sensed user-bioinformation and feature data corresponding to a label of each type of affect (delighted, surprise, anger, sorrow, fear, disgust, etc.) registered in the learning model are compared, and a label corresponding to feature data with high likelihood (similarity) is selected.

[6. About Embodiment of Execution of Highly Precise Affect Estimation Process]

Next, an embodiment in which a highly precise affect estimation process is executed is explained as a second embodiment.

As explained with reference to FIG. 18, the biometric-signal analyzing section 220 of the light-reception-signal analyzing section 104 depicted in FIG. 4 executes user-bioinformation analysis by selecting and extracting the subepidermal-tissue reflection light (diffuse light) from the light-reception signal of the light-receiving section 103.

As one of the bioinformation analysis process, analysis of the affect of the user (delighted, surprise, anger, sorrow, fear, disgust, etc.) can be performed.

The embodiment explained below is an embodiment in which highly precise affect analysis is performed further. Specifically, not only the analysis information of the biometric-signal analyzing section 220 of the light-reception-signal analyzing section 104 depicted in FIG. 4, but also a result of analysis by the facial-expression analyzing section 210 is used to execute highly precise affect analysis.

Figure 19:
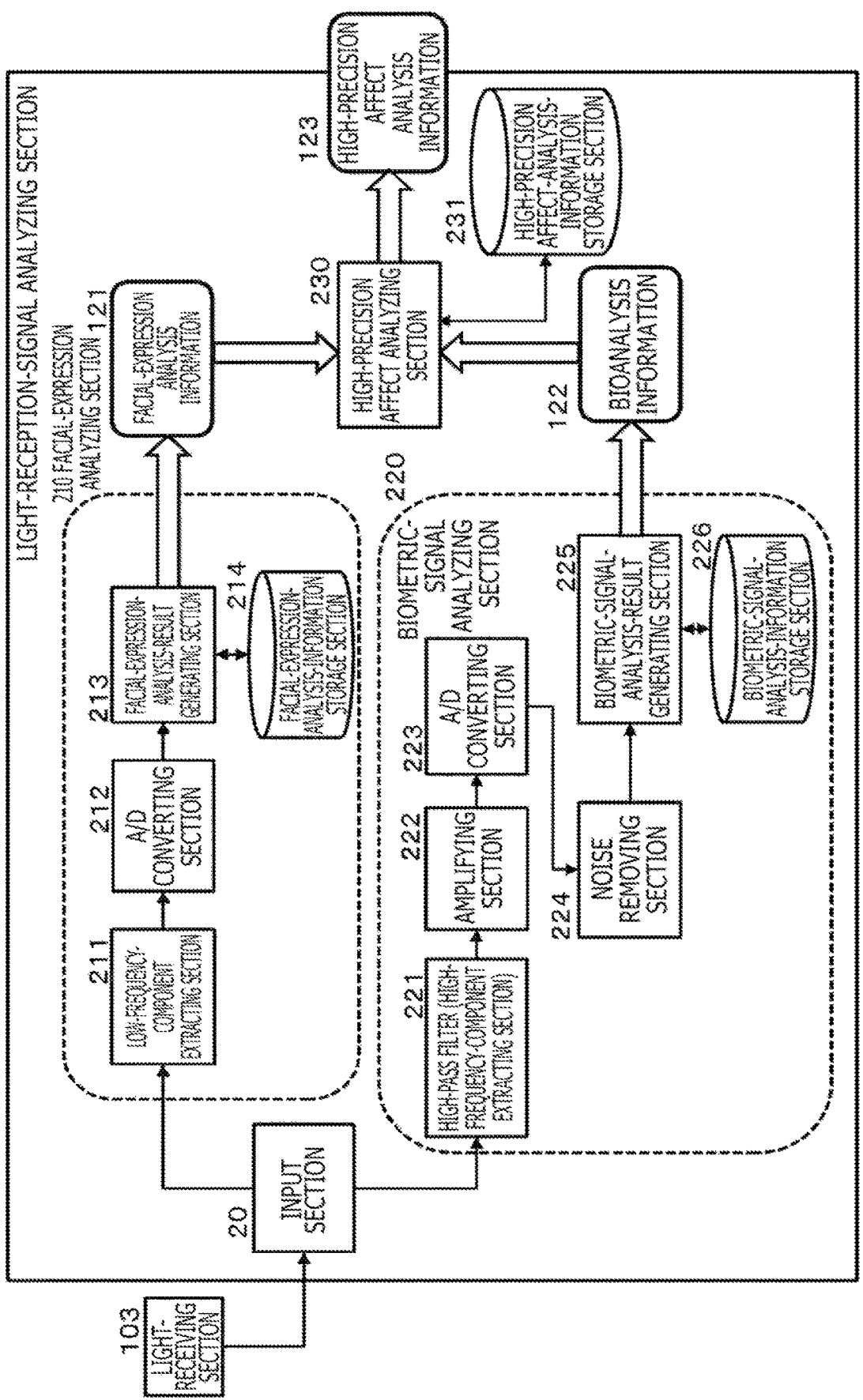
FIG. 19 is a figure for explaining a configuration example of the light-reception-signal analyzing section of the information processing apparatus of the present disclosure.

FIG. 19 is a figure depicting a configuration example of the light-reception-signal analyzing section 104 of the present second embodiment.

The light-reception-signal analyzing section 104 of the present second embodiment depicted in FIG. 19 has a configuration that is similar to that of the light-reception-signal analyzing section 104 depicted in FIG. 4 explained earlier, but additionally has a high-precision affect analyzing section 230 and a high-precision affect-analysis-information storage section 231.

The high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates and outputs high-precision affect analysis information 123.

The high-precision affect-analysis-information storage section 231 has stored thereon a learning model (affect model) generated by a learning process executed in advance. Specifically, feature data corresponding to each type of affect (a label of delighted, surprise, anger, sorrow, fear, disgust, or the like) is stored.

The high-precision affect-analysis-information storage section 231 stores a learning model in which feature data corresponding to a plurality of different affect states is associated. The feature data includes feature data of facial-expression information and feature data of bioinformation.

The high-precision affect analyzing section 230 performs a process of collating a result of analysis by using the facial-expression analysis information 121, which is a result of analysis by the facial-expression analyzing section 210, and the bioanalysis information 122, which is a result of analysis by the biometric-signal analyzing section 220, and the affect model stored on the high-precision affect-analysis-information storage section 231, and generates and outputs the high-precision affect analysis information 123.

In the present second embodiment, not only the user-bioinformation, but also the facial-expression information is taken into consideration to estimate affect.

An affect estimation process technique by using a facial expression is explained with reference.

Figure 20:
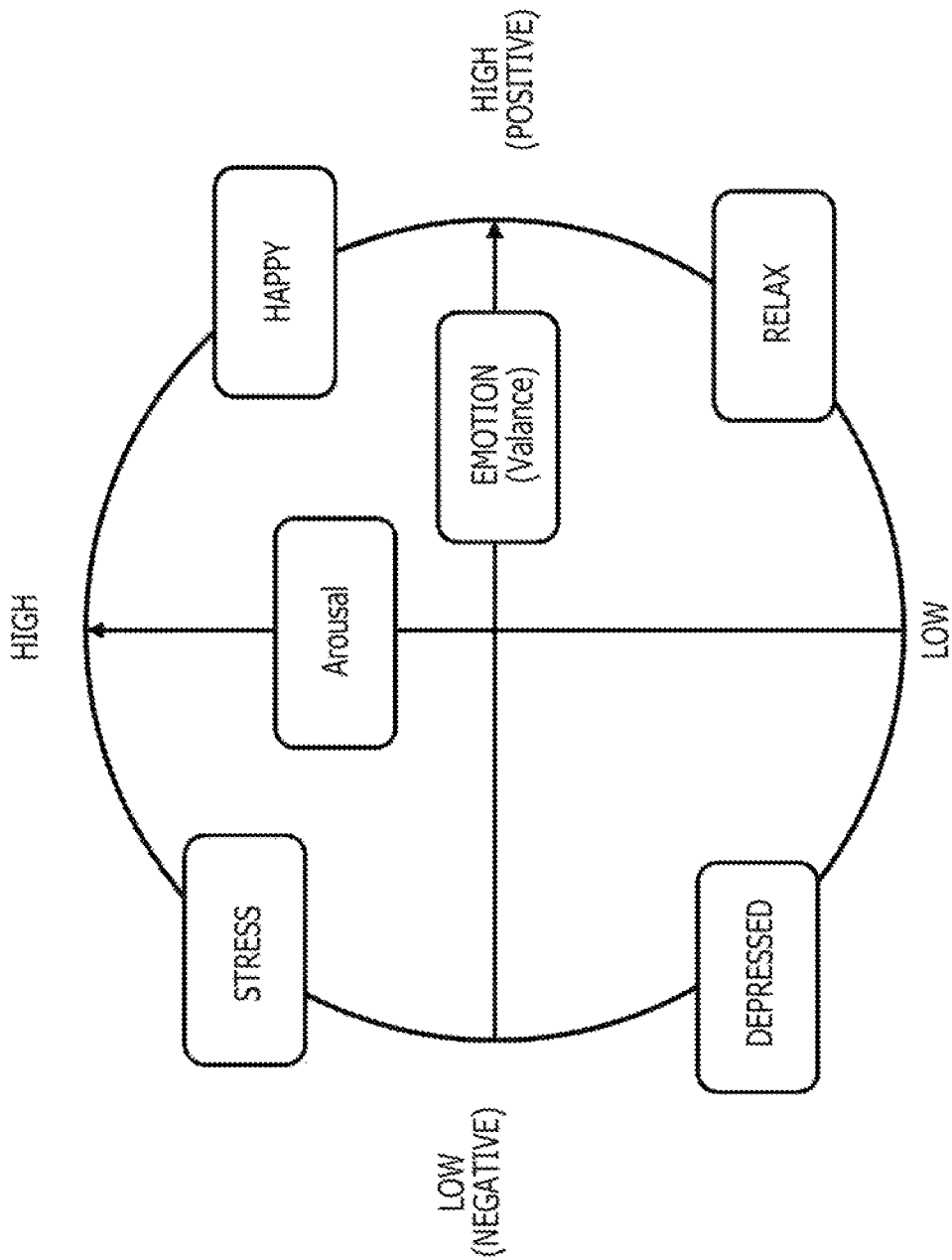
FIG. 20 is a figure for explaining the circumplex model of Russell.

FIG. 20 depicts the circumplex model of Russell (Russel).

The circumplex model of Russell is data that expresses affect (delighted, surprise, anger, sorrow, fear, disgust, etc.) which is the states of emotions of humans along the following two axes.

(1) Arousal
(2) Emotional valance (Valence) (positive/negative).

The vertical axis corresponds to A values representing arousal, and the horizontal axis corresponds to V values representing emotional valance (Valence) (positive/negative).

By using an AV value which is a combination an A value and a V value, it is possible to numerically represent affect (delighted, surprise, anger, sorrow, fear, disgust, etc.) which is the states of emotions of humans.

For example, in a case where affect is estimated from bioinformation (vital data), a normalized value) of the AV value is used. However, if affect is estimated only from bioinformation (vital data), correct information is not necessarily obtained, in some cases.

One of the reasons is that bioinformation is influenced not only by affect, but also by various factors.

Further, there is also another reason that, in the affect model (the circumplex model of Russell) explained with reference to FIG. 20, it is easy to estimate arousal from bioinformation, but it is difficult to estimate emotional valance (Valence) (positive/negative) only from bioinformation.

It becomes possible to highly precisely estimate emotional valance (Valence) (positive/negative) by using not only bioinformation, but also facial-expression information.

The second embodiment explained below is an embodiment in which not only bioinformation but also facial-expression information is used to highly precisely analyze the affect of a user.

FIGS. 21A and 21B are figures depicting execution sequences executed, by the information processing apparatus 100 of the present second embodiment, of a learning-model construction process by a learning process, and an affect analysis process by using the constructed learning model.

FIG. 21A AT TIME OF LEARNING is a figure depicting the sequence of the learning-model construction process by a learning process.

FIG. 21B AT TIME OF EXECUTION OF AFFECT ANALYSIS PROCESS is a figure depicting the execution sequence of the affect analysis process by using the constructed learning model.

First, FIG. 21A at the time of learning, the following data is input as input data.

(1) Facial-expression analysis information (facial-expression labels (1: serious look, 2: smile, 3: angry face, . . . ))
(2) Bioanalysis information (bioinformation feature amount)
(3) An AV value of a user (1) The facial-expression analysis information (facial-expression labels (1: serious look, 2: smile, 3: angry face, . . . )) is information obtained as a result of analysis at the facial-expression analyzing section 210.

(2) The bioanalysis information (bioinformation feature amount) is bioanalysis information obtained as a result of analysis at the biometric-signal analyzing section 220. Specifically, the bioanalysis information is bioinformation such as a blood flow rate, a blood flow speed, a pulse wave, a blood pressure, a heart rate, a heart rate fluctuation, a blood oxygen concentration, or arterial oxygen saturation.

(3) The AV value of a user is combined data of an A value representing arousal and a V value representing emotional valance (Valence) (positive/negative) in the circumplex model of Russell explained with reference to FIG. 20.

The data is acquired from a result of an answer to a question to the user about the emotional state, for example.

The input data, i.e., the following data, is input to a learner 421.
(1) Facial-expression analysis information (facial-expression labels (1: serious look, 2: smile, 3: angry face, . . . ))
(2) Bioanalysis information (bioinformation feature amount)
(3) An AV value of a user The learner 421 executes a learning process based on the input data. Specifically, a process of associating pieces of feature data, which are
(1) facial-expression analysis information (facial-expression labels (1: serious look, 2: smile, 3: angry face, . . . )), and
(2) bioanalysis information (bioinformation feature amount), with an AV value of the user is executed.

By this learning process, an affect model depicted as an output of FIG. 21A AT TIME OF LEARNING in FIGS. 21A and 21B, i.e., an affect model which is a learning model, is generated and is stored on the high-precision affect-analysis-information storage section 231.

The high-precision affect-analysis-information storage section 231 has recorded thereon feature data associated with affect labels (labels of delighted, surprise, anger, sorrow, fear, disgust, or the like) or AV values in the circumplex model of Russell explained with reference to FIG. 20.

The feature data includes facial-expression analysis information (facial-expression labels) and bioanalysis information (bioinformation feature amount).

FIG. 21B AT TIME OF EXECUTION OF AFFECT ANALYSIS PROCESS depicted in FIGS. 21A and 21B are figures depicting the execution sequence of the affect analysis process by using the constructed learning model.

Input data FIG. 21B at the time of execution of the affect analysis process is
(1) facial-expression analysis information (facial-expression labels (1: serious look, 2: smile, 3: angry face, . . . )), and
(2) bioanalysis information (bioinformation feature amount).

The input data is input to the high-precision affect analyzing section 230 of the light-reception-signal analyzing section 104.

As explained with reference to FIG. 19, the high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates and outputs the high-precision affect analysis information 123.

The facial-expression analysis information 121 which is a result of analysis by the facial-expression analyzing section 210 corresponds to the above-described input "(1) facial-expression analysis information (facial-expression labels (1: serious look, 2: smile, 3: angry face, . . . ))."

In addition, the bioanalysis information 122 which is a result of analysis by the biometric-signal analyzing section 220 corresponds to the above-described input "(2) bioanalysis information (bioinformation feature amount)."

The high-precision affect analyzing section 230 compares a feature amount (a facial-expression label and a biometric feature amount) that the input information has and feature data corresponding to the learning model recorded on the affect-analysis-information storage section 231, selects feature data determined as having the highest likelihood with the input signal, i.e., the most similar to the input signal, and selects and outputs affect information associated with the feature data, the affect information being, for example, affect information such as (delighted, surprise, anger, sorrow, fear, disgust, etc.) or an AV value which is an index value corresponding to affect.

In such a manner, at the time of execution of a high precision affect analysis process, a learning model (affect model) generated in advance is used to execute highly precise affect analysis of the user.

Next, a sequence of processes executed by the light-reception-signal analyzing section 104 depicted in FIG. 19 is explained with reference to a flowchart depicted in FIG. 22.

Figure 22:
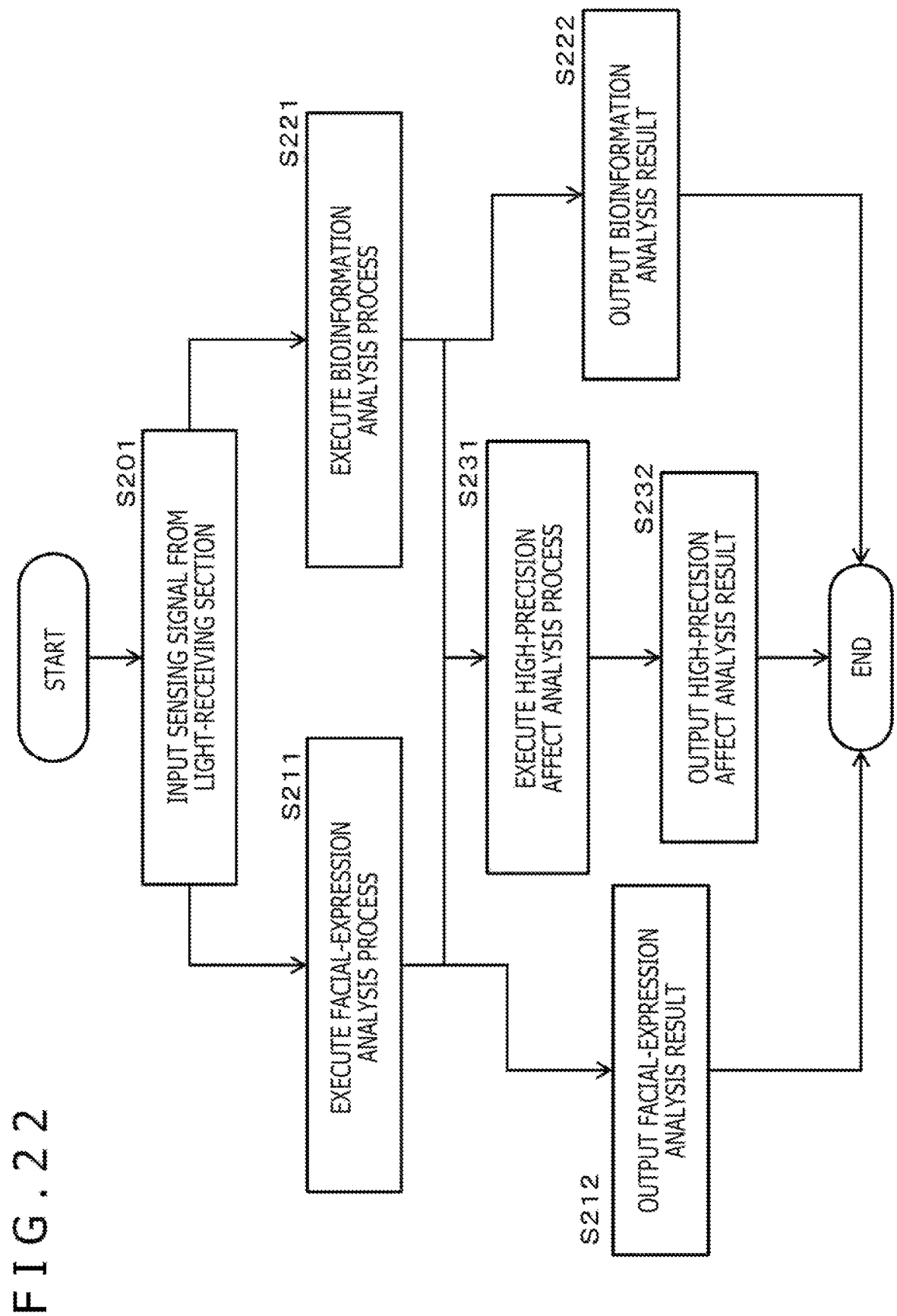
FIG. 22 is a figure depicting a flowchart for explaining a process sequence executed by the information processing apparatus of the present disclosure.

A process of each step in the flowchart depicted in FIG. 22 is explained sequentially.
(Step S201)

First, at Step S201, a light-reception signal of the light-receiving section 103 is input. Note that, as explained earlier, the light-reception signal of the light-receiving section 103 is a signal in which the following two types of reflection light are mixed.
(1) Skin-surface reflection light
(2) Subepidermal-tissue reflection light (diffuse light)
(Steps S211 and S212) Steps S211 and S212 are processes executed by the facial-expression analyzing section 210 depicted in FIG. 19.

The facial-expression analyzing section 210 executes user-facial-expression analysis by executing a process of selecting and extracting "(1) skin-surface reflection light" from the signal in which the above-described two types of signals are mixed and generates and outputs the facial-expression analysis information 121 as a result of the analysis.
(Steps S221 and S222)

Steps S221 and S222 are processes executed by the biometric-signal analyzing section 220 depicted in FIG. 19.

The biometric-signal analyzing section 220 executes user-bioinformation analysis by executing a process of selecting and extracting "(2) subepidermal-tissue reflection light (diffuse light)" from the signal in which the above-described two types of signals are mixed and generates and outputs the bioanalysis information 122 as a result of the analysis.
(Steps S231 and S232)

Steps S231 and S232 are processes executed by the high-precision affect analyzing section 230 depicted in FIG. 19. The high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates and outputs the high-precision affect analysis information 123.

This process is the process explained with reference to FIG. 21B earlier.

The high-precision affect analyzing section 230 performs a process of collating a result of the analysis by using the facial-expression analysis information 121, which is a result of analysis by the facial-expression analyzing section 210, and the bioanalysis information 122, which is a result of analysis by the biometric-signal analyzing section 220, and the affect model stored on the high-precision affect-analysis-information storage section 231, and generates and outputs the high-precision affect analysis information 123.

The high-precision affect-analysis-information storage section 231 has recorded thereon feature data associated with affect labels (labels of delighted, surprise, anger, sorrow, fear, disgust, or the like) or AV values in the circumplex model of Russell explained with reference to FIG. 20.

The feature data includes facial-expression analysis information (facial-expression labels) and bioanalysis information (bioinformation feature amount).

The high-precision affect analyzing section 230 selects a label (=an affect label (a label of delighted, surprise, anger, sorrow, fear, disgust, or the like)) or an AV value, the label or the AV value having a feature amount which is the closest to the feature amount of the facial-expression analysis information 121 which is a result of analysis by the facial-expression analyzing section 210 and the bioanalysis information 122 which is a result of analysis by the biometric-signal analyzing section 220, and outputs the selected the label or AV value as the high-precision affect analysis information 123.

[7. About Use Examples of Results of Analysis by Information Processing Apparatus of Present Disclosure]

Next, use examples of results of analysis by the information processing apparatus of the present disclosure is explained.

The following plural process examples are explained.
(1) Process Example of Use for Game Event Control
(2) Process Example of Use for Authenticity Determination about User Facial Expression
(3) Process Example of Use for Mimetic-Muscle Training by User
(4) Process Example of Use for Avatar Control
(5) Process Example of Use for Determination about User Spirit

[7-(1) Process Example of Use for Game Event Control]

First, a process example of use of a result of analysis by the information processing apparatus of the present disclosure for game event control is explained.

Figure 23:
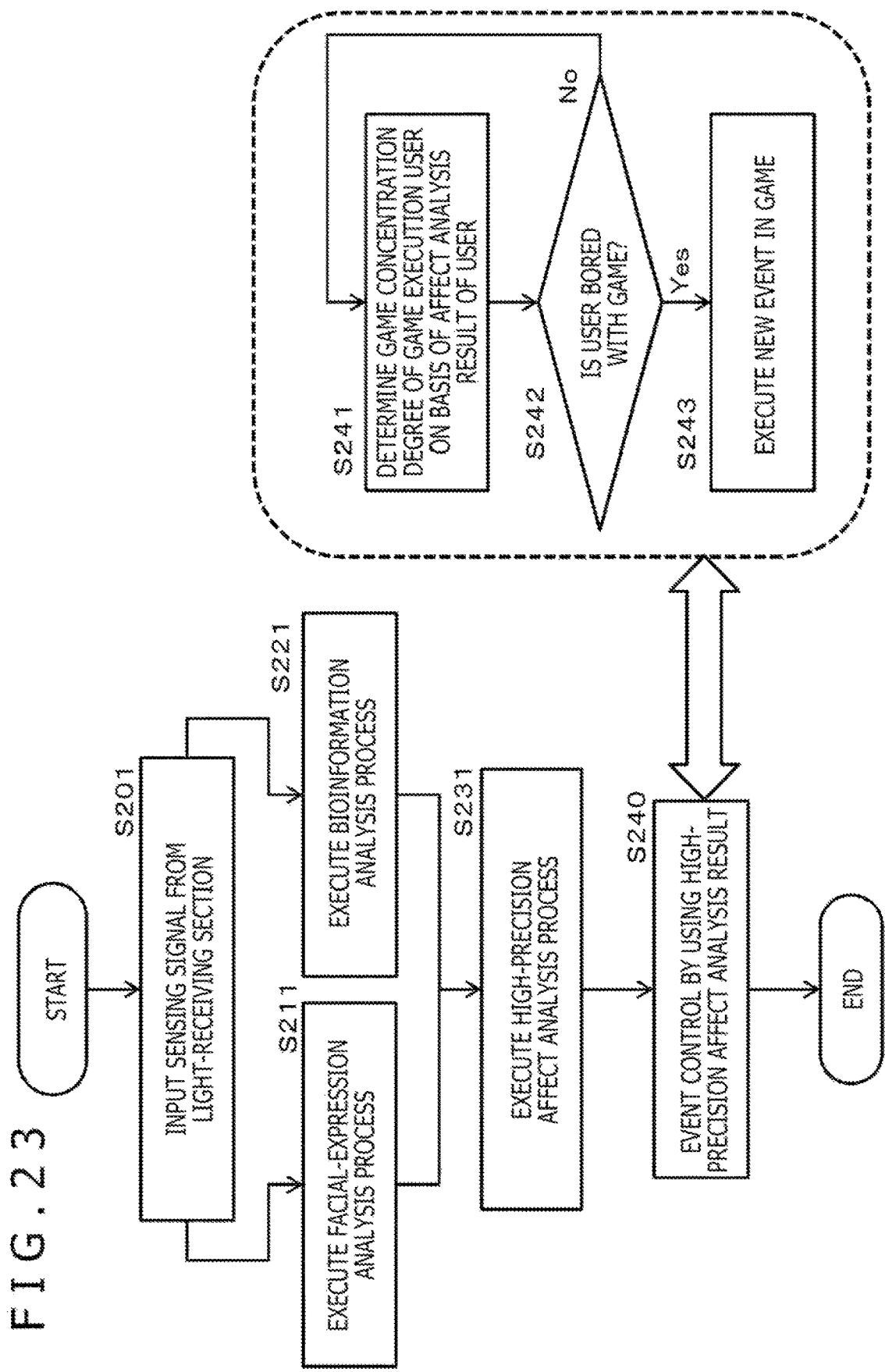
FIG. 23 is a figure depicting a flowchart for explaining a process sequence executed by the information processing apparatus of the present disclosure.

FIG. 23 is a flowchart for explaining a process sequence of this process example.

A process of each step in the flowchart depicted in FIG. 23 is explained. Note that processes at Steps S201, S211, S221, and S231 in the flowchart depicted in FIG. 23 are processes similar to the processes at Steps S201, S211, S221, and S231 in the flow explained with reference to FIG. 22 earlier.

It should be noted that, however, a user to be the affect analysis target here is a user who is executing a game.

(Steps S201 to S231)

At Step S201, a light-reception signal of the light-receiving section 103 is input. Note that, as explained earlier, the light-reception signal of the light-receiving section 103 is a signal in which the following two types of reflection light are mixed.

(1) Skin-surface reflection light
(2) Subepidermal-tissue reflection light (diffuse light)

Step S211 is a process executed by the facial-expression analyzing section 210 depicted in FIG. 19.

The facial-expression analyzing section 210 executes user-facial-expression analysis by executing a process of selecting and extracting "(1) skin-surface reflection light" from the signal in which the above-described two types of signals are mixed, generates the facial-expression analysis information 121 as a result of the analysis, and outputs the facial-expression analysis information 121 to the high-precision affect analyzing section 230.

Step S221 is a process executed by the biometric-signal analyzing section 220 depicted in FIG. 19.

The biometric-signal analyzing section 220 executes user-bioinformation analysis by executing a process of selecting and extracting "(2) subepidermal-tissue reflection light (diffuse light)" from the signal in which the above-described two types of signals are mixed, generates the bioanalysis information 122 as a result of the analysis, and outputs the bioanalysis information 122 to the high-precision affect analyzing section 230.

Step S231 is a process executed by the high-precision affect analyzing section 230 depicted in FIG. 19. The high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates the high-precision affect analysis information 123.

(Step S240)

Step S240 is a process that uses the high-precision affect analysis information 123 generated by the high-precision affect analyzing section 230, and, in this process example, is a process executed by a game control section.

The game control section receives, as an input, the high-precision affect analysis information 123 generated by the high-precision affect analyzing section 230 and executes processes at Steps S241 to S243 depicted in the figure.

(Step S241)

First, at Step S241, the game control section receives, as an input, an affect analysis result of the game execution user and determines the degree of concentration of the user on the game on the basis of the input affect analysis result.

(Step S242)

At Step S242, as a result of the process of the determination about the degree of concentration on the game at Step S241, it is determined whether or not the user is bored with the game.

In a case where it is determined that the user is not bored with the game, the process returns to Step S241, and the determination about the degree of concentration of the user on the game based on the affect analysis result of the user is continued.

On the other hand, in a case where it is determined that the user is bored with the game, the process proceeds to Step S243.

(Step S243)

In a case where it is determined at Step S242 that the user is bored with the game, the process proceeds to Step S233.

At Step S243, the game control section executes control of generating a new event in the game.

For example, a process of generating an event such as a stage change or the appearance of a new character is performed.

By performing game control based on the affect of the game execution user in such a manner, it becomes possible to present game development that does not make the user bored.

[7-(2) Process Example of Use for Authenticity Determination about User Facial Expression]

Next, a process example of use of a result of analysis by the information processing apparatus of the present disclosure for an authenticity determination about a user facial expression is explained.

A result of analysis of a user facial expression is obtained by a facial-expression analysis process. For example, a determination that a user facial expression is a smile, etc., is obtained. However, the smile may be a fake smile which is against the true emotion of the user, in some cases.

The process example explained below is a process example in which distinctions are made between such fake smiles and genuine smiles and the like, i.e., a process example in which a determination is made whether or not a user facial expression is a true facial expression reflecting the emotion of the user.

Figure 24:
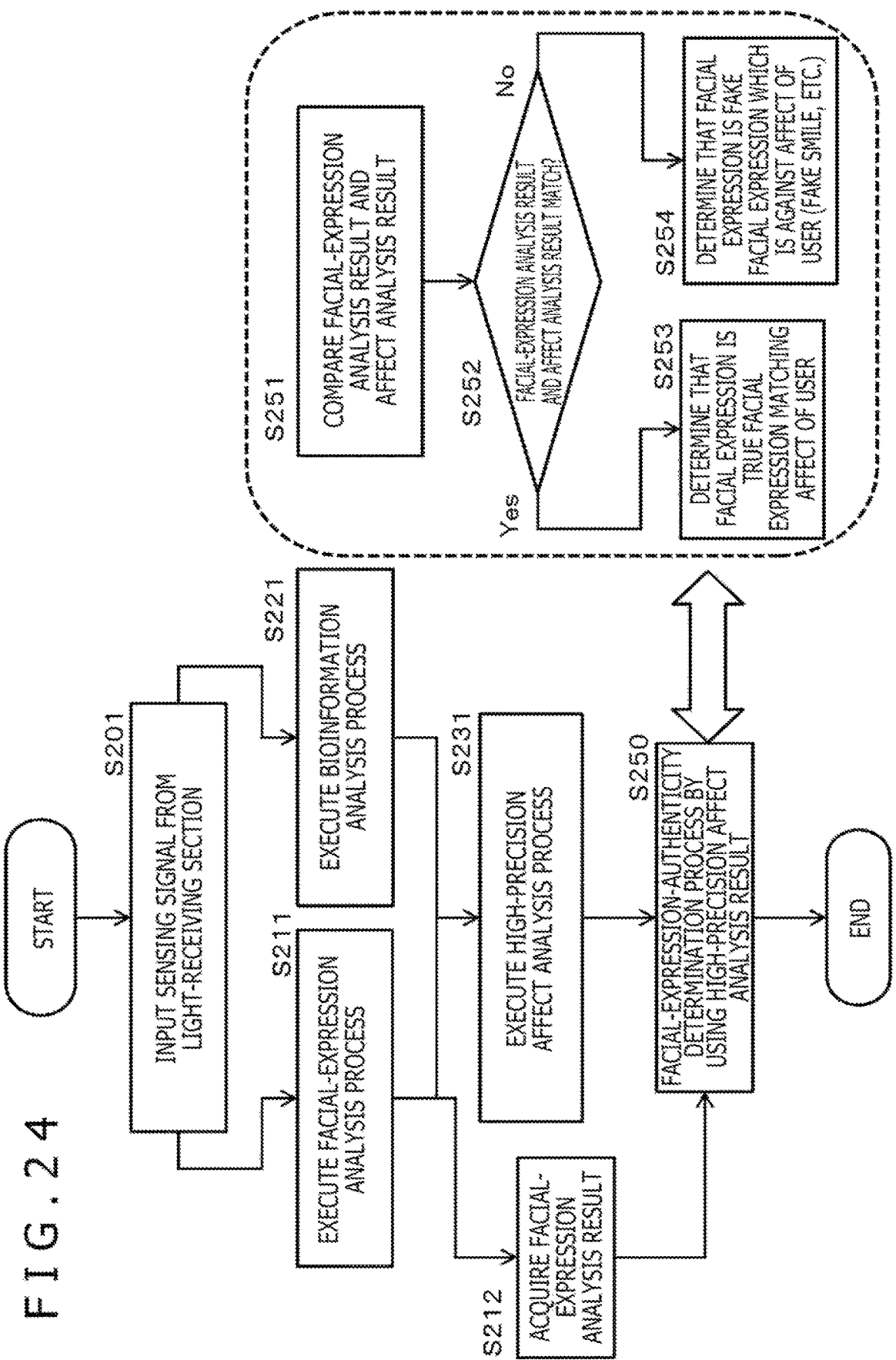
FIG. 24 is a figure depicting a flowchart for explaining a process sequence executed by the information processing apparatus of the present disclosure.

FIG. 24 is a flowchart for explaining a process sequence of this process example.

A process of each step in the flowchart depicted in FIG. 24 is explained. Note that processes at Steps S201, S211, S212, S221, and S231 in the flowchart depicted in FIG. 24 are processes similar to the processes at Steps S201, S211, S212, S221, and S231 in the flow explained with reference to FIG. 22 earlier.

(Steps S201 to S231)

At Step S201, a light-reception signal of the light-receiving section 103 is input. Note that, as explained earlier, the light-reception signal of the light-receiving section 103 is a signal in which the following two types of reflection light are mixed.

(1) Skin-surface reflection light
(2) Subepidermal-tissue reflection light (diffuse light)

Steps S211 and S212 are processes executed by the facial-expression analyzing section 210 depicted in FIG. 19.

The facial-expression analyzing section 210 executes user-facial-expression analysis by executing a process of selecting and extracting "(1) skin-surface reflection light" from the signal in which the above-described two types of signals are mixed, generates the facial-expression analysis information 121 as a result of the analysis, outputs the facial-expression analysis information 121 to the high-precision affect analyzing section 230, and further outputs the facial-expression analysis information 121 also to a facial-expression authenticity determining section that executes a process at Step S250.

Step S221 is a process executed by the biometric-signal analyzing section 220 depicted in FIG. 19.

The biometric-signal analyzing section 220 executes user-bioinformation analysis by executing a process of selecting and extracting "(2) subepidermal-tissue reflection light (diffuse light)" from the signal in which the above-described two types of signals are mixed, generates the bioanalysis information 122 as a result of the analysis, and outputs the bioanalysis information 122 to the high-precision affect analyzing section 230.

Step S231 is a process executed by the high-precision affect analyzing section 230 depicted in FIG. 19. The high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates the high-precision affect analysis information 123.

(Step S250)

Step S250 is a process that uses the facial-expression analysis information 121 generated by the facial-expression analyzing section 210 and the high-precision affect analysis information 123 generated by the high-precision affect analyzing section 230, and, in this process example, is a process executed by the facial-expression authenticity determining section that determines the authenticity of a user facial expression.

The facial-expression authenticity determining section receives, as inputs, the facial-expression analysis information 121 generated by the facial-expression analyzing section 210 and the high-precision affect analysis information 123 generated by the high-precision affect analyzing section 230, and executes processes at Steps S251 to S253 depicted in the figure.

(Step S251)

First, at Step S251, the facial-expression authenticity determining section compares the facial-expression analysis information 121 generated by the facial-expression analyzing section 210 and the high-precision affect analysis information 123 generated by the high-precision affect analyzing section 230.

(Step S252)

At Step S252, it is determined, as a result of the comparison at Step S251, whether the facial-expression analysis information 121 and the high-precision affect analysis information 123 match or do not match.

In a case where the facial-expression analysis information 121 generated by the facial-expression analyzing section 210 and the high-precision affect analysis information 123 generated by the high-precision affect analyzing section 230 match, the process proceeds to Step S253.

On the other hand, in a case where the facial-expression analysis information 121 generated by the facial-expression analyzing section 210 and the high-precision affect analysis information 123 generated by the high-precision affect analyzing section 230 do not match, the process proceeds to Step S254.

(Step S253)

In a case where, at Step S252, the facial-expression analysis information 121 generated by the facial-expression analyzing section 210 and the high-precision affect analysis information 123 generated by the high-precision affect analyzing section 230 match, the process proceeds to Step S253.

At Step S253, the facial-expression authenticity determining section determines that the user facial expression is a true facial expression reflecting the affect of the user.

(Step S254)

On the other hand, in a case where, at Step S252, the facial-expression analysis information 121 generated by the facial-expression analyzing section 210 and the high-precision affect analysis information 123 generated by the high-precision affect analyzing section 230 do not match, the process proceeds to Step S254.

At Step S254, the facial-expression authenticity determining section determines that the user facial expression is a false facial expression not reflecting the affect of the user.

By comparing the user facial expression and affect in such a manner, it becomes possible to determine whether or not the user facial expression is a true facial expression reflecting the state of the mind.

[7-(3) Process Example of Use for Mimetic-Muscle Training by User]

Next, a process example of use of a result of analysis by the information processing apparatus of the present disclosure for mimetic-muscle training by a user is explained.

Figure 25:
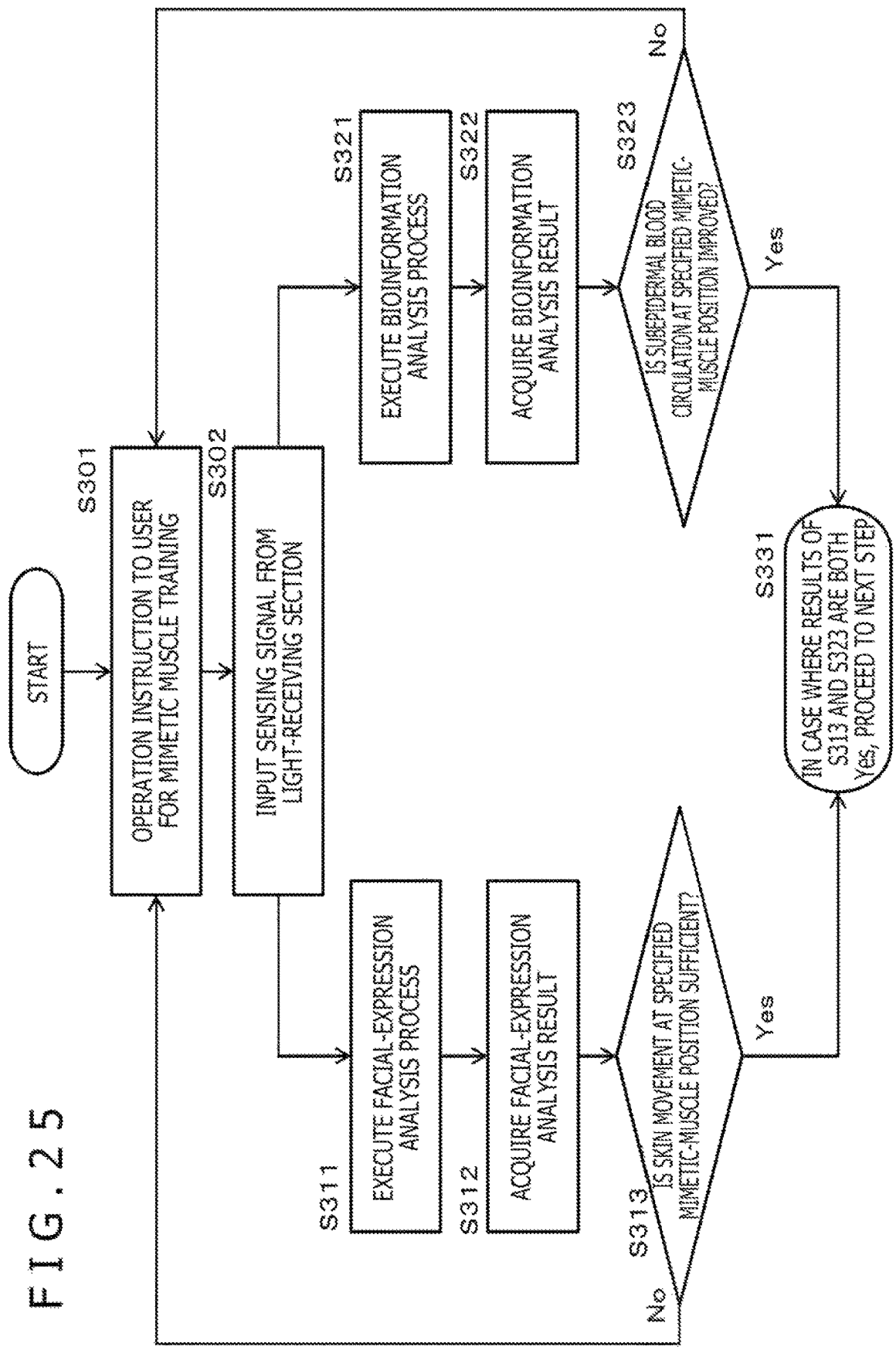
FIG. 25 is a figure depicting a flowchart for explaining a process sequence executed by the information processing apparatus of the present disclosure.

FIG. 25 is a flowchart for explaining a process sequence of this process example.

A process of each step in the flowchart depicted in FIG. 25 is explained. Note that a user to be the affect analysis target here is a user who is training his/her mimetic muscles.

(Step S301)

First, at Step S301, the user is given an instruction to start particular mimetic-muscle training.

Specifically, an instruction is given to move one certain mimetic muscle.

(Steps S302 to S322)

At Step S302, a light-reception signal of the light-receiving section 103 is input. Note that, as explained earlier, the light-reception signal of the light-receiving section 103 is a signal in which the following two types of reflection light are mixed.

(1) Skin-surface reflection light
(2) Subepidermal-tissue reflection light (diffuse light)

Steps S311 and S312 are processes executed by the facial-expression analyzing section 210 depicted in FIG. 19.

The facial-expression analyzing section 210 executes user-facial-expression analysis by executing a process of selecting and extracting "(1) skin-surface reflection light" from the signal in which the above-described two types of signals are mixed, generates the facial-expression analysis information 121 as a result of the analysis, and outputs the facial-expression analysis information 121 to the mimetic-muscle training-state analyzing section.

Steps S321 and S322 are processes executed by the biometric-signal analyzing section 220 depicted in FIG. 19.

The biometric-signal analyzing section 220 executes user-bioinformation analysis by executing a process of selecting and extracting "(2) subepidermal-tissue reflection light (diffuse light)" from the signal in which the above-described two types of signals are mixed, generates the bioanalysis information 122 as a result of the analysis, and outputs the bioanalysis information 122 to the mimetic-muscle training-state analyzing section.

(Step S313)

Step S313 is a process executed by the mimetic-muscle training-state analyzing section.

The mimetic-muscle training-state analyzing section analyzes the facial-expression analysis information 121 input from the facial-expression analyzing section 210 and determines whether or not the user is moving the mimetic muscle as instructed.

That is, it is determined whether or not the skin movement is sufficient.

In a case where it is determined that the skin movement is not sufficient, the process returns to Step S301, and the instruction to move the same mimetic muscle is continued.

On the other hand, in a case where it is determined that the skin movement is sufficient, the process proceeds to Step S331.

(Step S323)

Step S323 is also a process executed by the mimetic-muscle training-state analyzing section.

The mimetic-muscle training-state analyzing section analyzes the bioanalysis information 122 input from the biometric-signal analyzing section 220 and determines whether or not the subepidermal blood circulation at the mimetic-muscle position specified for the user is improved.

In a case where it is determined that the subepidermal blood circulation is not improved, the process returns to Step S301, and the instruction to move the same mimetic muscle is continued.

On the other hand, in a case where it is determined that the subepidermal blood circulation at the specified mimetic-muscle position is improved, the process proceeds to Step S331.

(Step S331)

Step S331 is a process to be executed in a case where results of the determinations at Step S313 and S323 are Yes, i.e., it is determined that the skin movement is sufficient and where it is determined that the subepidermal blood circulation at the specified mimetic-muscle position is improved.

In this case, the mimetic-muscle training-state analyzing section proceeds to the next Step such as giving an instruction to move a different mimetic muscle.

By analyzing both the facial expression and a living form of the mimetic-muscle training user in such a manner, it becomes possible to make the user execute surer mimetic-muscle trainings.

Note that, not being limited to mimetic-muscle trainings, it is also possible to give an effective instruction for making a predetermined facial expression of a face like making a facial expression such as a smile, for example, by giving an instruction to move a predetermined muscle.

[7-(4) Process Example of Use for Avatar Control]

Next, a process example of use of a result of analysis by the information processing apparatus of the present disclosure for avatar control is explained.

This process example is a process example in which control to display an avatar reflecting a facial expression and an emotion of a user is performed.

Figure 26:
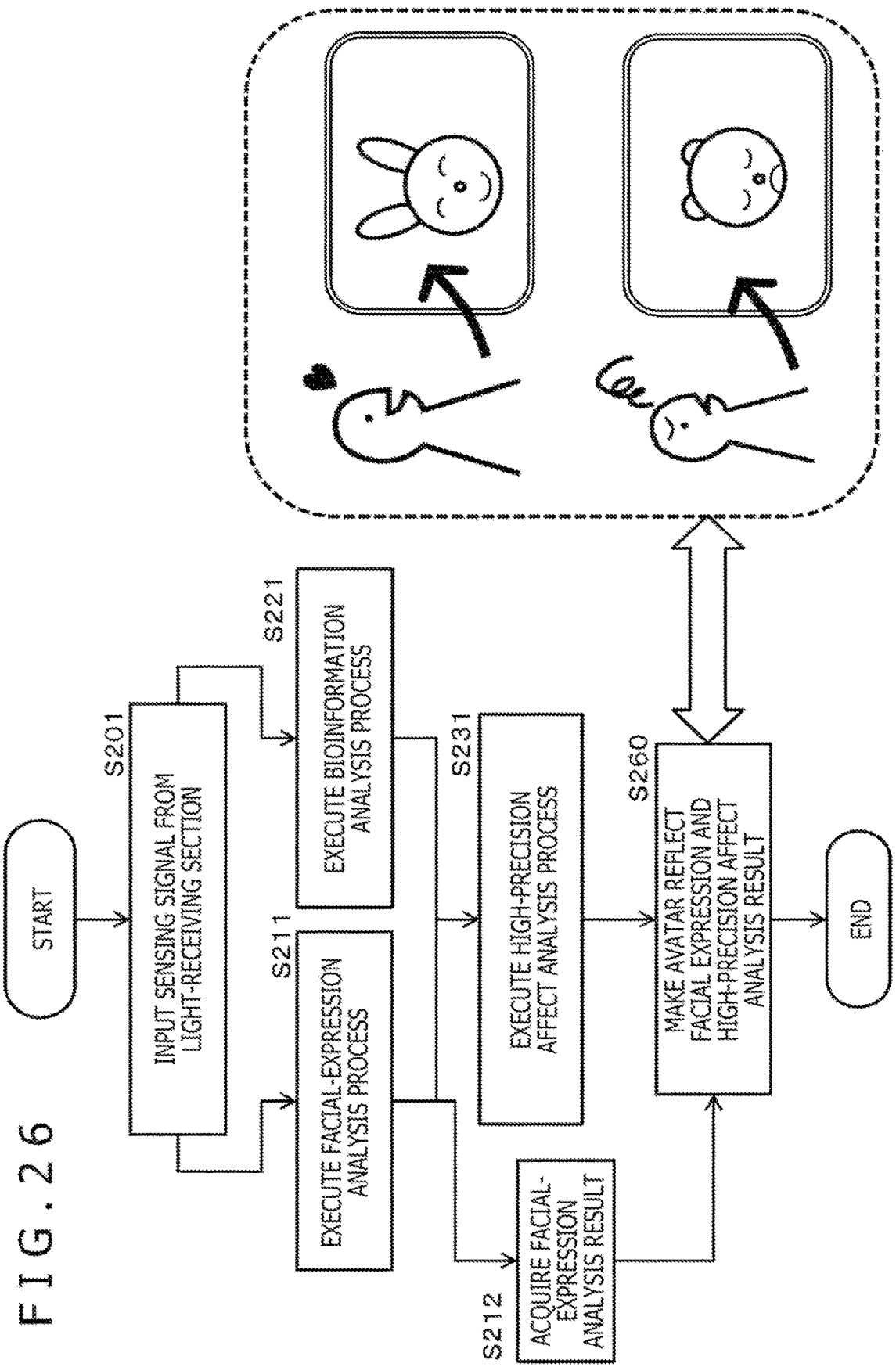
FIG. 26 is a figure depicting a flowchart for explaining a process sequence executed by the information processing apparatus of the present disclosure.

FIG. 26 is a flowchart for explaining a process sequence of this process example.

A process of each step in the flowchart depicted in FIG. 26 is explained. Note that processes at Steps S201, S211, S212, S221, and S231 in the flowchart depicted in FIG. 26 are processes similar to the processes at Steps S201, S211, S212, S221, and S231 in the flow explained with reference to FIG. 22 earlier.

(Steps S201 to S231)

At Step S201, a light-reception signal of the light-receiving section 103 is input. Note that, as explained earlier, the light-reception signal of the light-receiving section 103 is a signal in which the following two types of reflection light are mixed.

(1) Skin-surface reflection light
(2) Subepidermal-tissue reflection light (diffuse light)

Steps S211 and S212 are processes executed by the facial-expression analyzing section 210 depicted in FIG. 19.

The facial-expression analyzing section 210 executes user-facial-expression analysis by executing a process of selecting and extracting "(1) skin-surface reflection light" from the signal in which the above-described two types of signals are mixed, generates the facial-expression analysis information 121 as a result of the analysis, outputs the facial-expression analysis information 121 to the high-precision affect analyzing section 230, and further outputs the facial-expression analysis information 121 also to a facial-expression authenticity determining section that executes a process at Step S250.

Step S221 is a process executed by the biometric-signal analyzing section 220 depicted in FIG. 19.

The biometric-signal analyzing section 220 executes user-bioinformation analysis by executing a process of selecting and extracting "(2) subepidermal-tissue reflection light (diffuse light)" from the signal in which the above-described two types of signals are mixed, generates the bioanalysis information 122 as a result of the analysis, and outputs the bioanalysis information 122 to the high-precision affect analyzing section 230.

Step S231 is a process executed by the high-precision affect analyzing section 230 depicted in FIG. 19. The high-precision affect analyzing section 230 receives, as inputs, the facial-expression analysis information 121 which is a result of analysis by the facial-expression analyzing section 210 and the bioanalysis information 122 which is a result of analysis by the biometric-signal analyzing section 220, and generates the high-precision affect analysis information 123.

(Step S260)

Step S260 is a process that uses the facial-expression analysis information 121 generated by the facial-expression analyzing section 210 and the high-precision affect analysis information 123 generated by the high-precision affect analyzing section 230, and, in this process example, is a process executed by an avatar control section that performs avatar control used by a user.

The avatar control section receives, as inputs, the facial-expression analysis information 121 generated by the facial-expression analyzing section 210 and the high-precision affect analysis information 123 generated by the high-precision affect analyzing section 230, and performs a process of changing the facial expression and the like of an avatar that is caused to be displayed on a PC or a smartphone by a user, the avatar corresponding to the user.

For example, in a case where the user is smiling and has affect of a delighted state, an avatar that is smiling and looks like having fun is displayed.

On the other hand, in a case where the user has a sad face and has affect of a sad state as well, an avatar that has a sad face and looks gloomy is displayed.

Further, it is also possible to perform processes like the ones below.

If the affect of the user is in a highly excited state when a smile is sensed, an avatar who has a delighted facial expression and is jumping around is displayed. On the other hand, if the affect of the user is in a relatively serene state when a smile is sensed, an avatar who is smiling gently with calm gestures is displayed.

In such a manner, it becomes possible to express a wide variety of states of a user that cannot be realized only by sensing of facial expressions.

In such a manner, in this process example, it becomes possible to cause an avatar reflecting facial expressions and affect of a user to be displayed.

[7-(5) Process Example of Use for Determination about User Spirit]

Next, a process example of use of a result of analysis by the information processing apparatus of the present disclosure for a determination about user spirit is explained.

This process example is a process example in which user spirit is determined on the basis of a facial expression and an emotion of a user.

In a case where this process example is executed, it becomes necessary to construct a model that makes it possible to perform a spirit determination as a learning model.

FIGS. 27A and 27B are figure depicting execution sequences of a learning-model (spirit-model) construction process by a learning process and a spirit analysis process by using the constructed learning model.

FIG. 27A AT TIME OF LEARNING is a figure depicting the sequence of the learning-model construction process by a learning process.

FIG. 27B AT TIME OF EXECUTION OF SPIRIT ANALYSIS PROCESS is a figure depicting the execution sequence of the spirit analysis process by using the constructed learning model.

First, FIG. 27A at the time of learning, the following data is input as input data.

(1) Light-receiving-section-output time-series data (multi-channel: S1, S2, . . . )

"(1) Light-receiving-section-output time-series data (multi-channel: S1, S2, . . . )" is time-series data of output signals from the sensors attached to the HMD, for example. That is, it is data such as the signals S1 to S7 explained with reference to FIG. 10 earlier.

The light-reception-signal analyzing section 104 generates and outputs the facial-expression analysis result and the bioinformation analysis result, on the basis of the input data.

These results are input to a learner (spirit model generating section) 450.

The learner (spirit model generating section) 450 receives, as inputs, the facial-expression analysis result and the bioinformation analysis result, generates a spirit model which is a learning model in which spirit levels and the information are associated, and stores the spirit model on the spirit-analysis information storage section 470.

FIG. 27B AT TIME OF EXECUTION OF SPIRIT ANALYSIS PROCESS depicted in FIGS. 27A and 27B are figures depicting the execution sequence of the facial-expression analysis process by using the constructed learning model (spirit model).

Input data FIG. 27B at the time of execution of the spirit analysis process is (1) light-receiving-section-output time-series data (multi-channel: S1, S2, . . . ).

The input data is input to the light-reception-signal analyzing section 104.

The light-reception-signal analyzing section 104 generates and outputs the facial-expression analysis result and the bioinformation analysis result, on the basis of the input data.

These results are input to a spirit determining section 480.

The spirit determining section 480 refers to the learning model recorded on the spirit-analysis information storage section 470, i.e., the learning model (spirit model) in which feature data of facial-expression information and bioinformation is associated with various spirit levels, selects feature data determined as being the most similar to the input signal, and selects and outputs a spirit level associated with the feature data.

Output data FIG. 27B at the time of execution of the facial-expression analysis process is (1) data representing whether or not the user is spirited or the level of spirit.

Note that, while, in the configuration example depicted in and explained with reference to FIGS. 27A and 27B, the learning model (spirit model) in which the feature data of the facial-expression information and the bioinformation is associated with the various spirit levels is used to determine the spirit level of a user, it becomes possible to determine not only the spirit level, but also various states of the user by changing the learning model to be used.

For example, by generating and using a learning model in which the feature data of the facial-expression information and the bioinformation is associated with various state levels of a user such as an excitement level, a delighted level, a sorrow level, or a depression level, determinations of various user states become possible.

[8. About Hardware Configuration Example of Information Processing Apparatus]

Next, a hardware configuration example of the information processing apparatus 100 of the present disclosure is explained.

Figure 28:
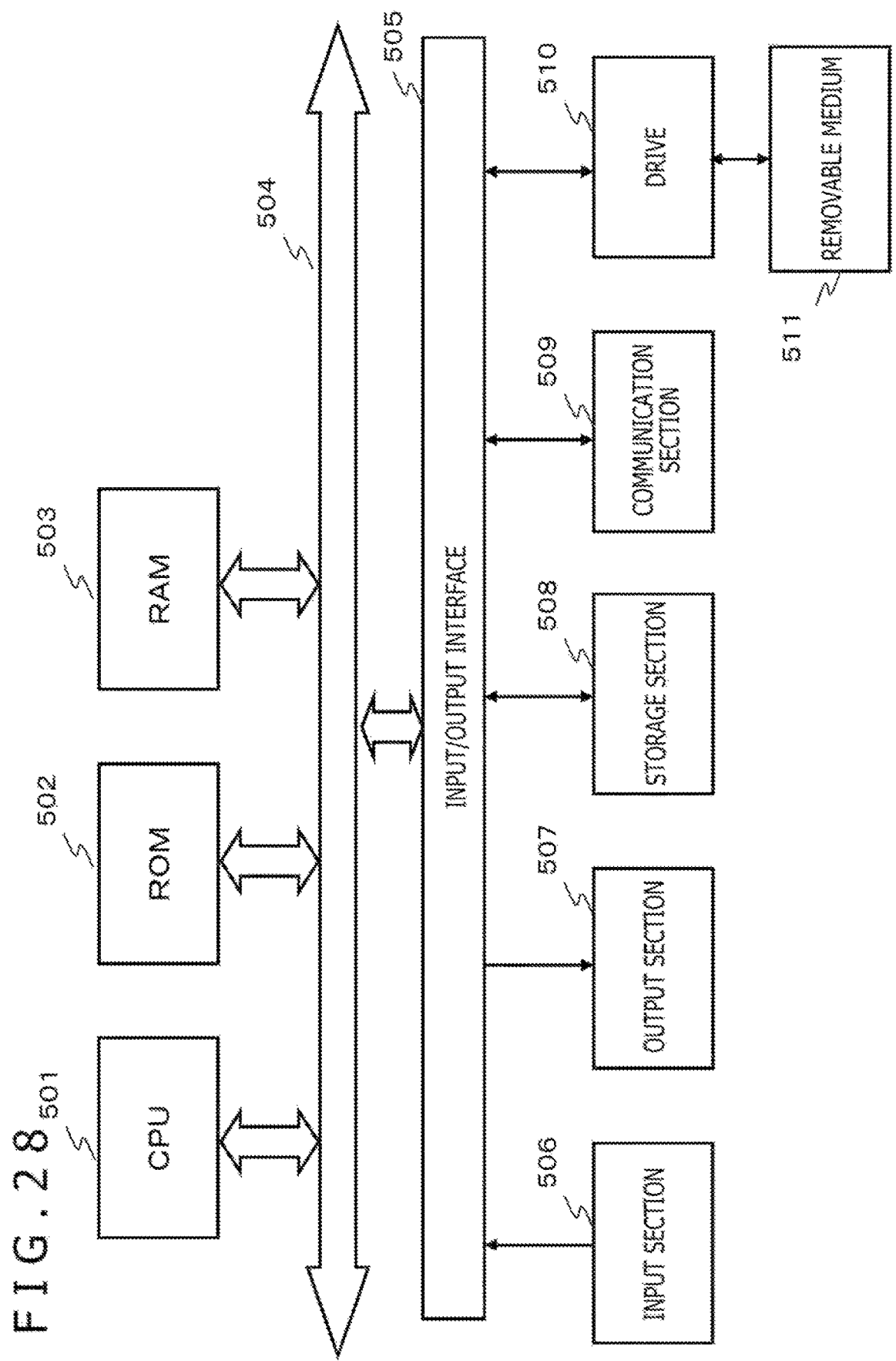
FIG. 28 is a figure for explaining a hardware configuration example of the information processing apparatus of the present disclosure.

FIG. 28 is a figure depicting the hardware configuration example of the information processing apparatus.

A CPU (Central Processing Unit) 501 functions as a data processing section that executes various types of processes according to a program stored on a ROM (Read Only Memory) 502 or a storage section 508. For example, the CPU 501 executes the processes according to the sequences explained in the embodiments mentioned above.

A RAM (Random Access Memory) 503 stores programs executed by the CPU 501, data, and the like. The CPU 501, the ROM 502, and the RAM 503 are interconnected by a bus 504.

The CPU 501 is connected to an input/output interface 505 via the bus 504. The input/output interface 505 is connected with an input section 506 including various types of switches, a keyboard, a touch panel, a mouse, a microphone, and further a status data acquiring section such as sensors, and with an output section 507 including a display, a speaker, and the like.

The CPU 501 receives, as inputs, commands, status data, and the like input from the input section 506, executes various types of processes, and outputs processing results to the output section 507, for example.

The storage section 508 connected to the input/output interface 505 includes a hard disk and the like, for example, and stores programs to be executed by the CPU 501 and various types of data. A communication section 509 functions as a transmitting/receiving section for data communication via networks such as the Internet or a local area network and communicates with an external apparatus.

A drive 510 connected to the input/output interface 505 drives a removable medium 511 such as a magnetic disc, an optical disc, a magneto-optical disc, or a semiconductor memory such as a memory card and executes recording or reading of data.

[9. Summary of Configuration of Present Disclosure]

Thus far, the embodiments of the present disclosure are explained in detail with reference to the particular embodiments. However, it is obvious that those skilled in the art can make modification or use substitutes in the embodiments within the scope not deviating from the gist of the present disclosure. That is, the present invention has been disclosed in exemplary forms, and should not be interpreted in a limited manner. In order to decide the gist of the present disclosure, the section of claims should be considered.

Note that the technology disclosed in the present specification can have configurations like the ones below.

(1) An information processing apparatus including:
a light-receiving section that receives reflection light of light emitted to a user face; and
a light-reception-signal analyzing section that analyzes a light-reception signal of the light-receiving section, in which
the light-reception-signal analyzing section has
a facial-expression analyzing section that generates facial-expression analysis information on the basis of the reflection light, and
a biometric-signal analyzing section that generates bioanalysis information on the basis of the reflection light.

(2) The information processing apparatus according to (1), in which
the light-reception signal of the light-receiving section includes skin-surface reflection light and subepidermal-tissue reflection light,
the facial-expression analyzing section extracts a low frequency component from the light-reception signal of the light-receiving section, acquires the skin-surface reflection light, and executes facial-expression analysis, and
the biometric-signal analyzing section extracts a high frequency component from the light-reception signal of the light-receiving section, acquires the subepidermal-tissue reflection light, and executes a biometric-signal analysis process.

(3) The information processing apparatus according to (1) or (2), in which the facial-expression analyzing section executes a facial-expression analysis process by referring to a learning model stored on a storage section.

(4) The information processing apparatus according to (3), in which the learning model has corresponding data of facial-expression labels and feature data of skin-surface reflection-light signals reflecting skin-surface movements, the facial-expression labels corresponding to a plurality of different facial expressions.

(5) The information processing apparatus according to any of (1) to (4), in which the biometric-signal analyzing section executes a bioanalysis process by referring to a learning model stored on a storage section.

(6) The information processing apparatus according to (5), in which the learning model has corresponding data of feature data of subepidermal reflection-light signals reflecting subepidermal states corresponding to a plurality of different biological states.

(7) The information processing apparatus according to any of (1) to (6), in which the biometric-signal analyzing section analyzes subepidermal reflection light of a user and generates bioanalysis information regarding at least any of a blood flow rate, a blood flow speed, a pulse wave, a blood pressure, a heart rate, a heart rate fluctuation, a blood oxygen concentration, and arterial oxygen saturation.

(8) The information processing apparatus according to any of (1) to (7), in which the light-receiving section is attached at a plurality of positions of a head-mounted display.

(9) The information processing apparatus according to any of (1) to (8), in which the light-reception-signal analyzing section executes analysis of reflection light from a plurality of different positions on the user face.

(10) The information processing apparatus according to any of (1) to (9), in which
the light-reception-signal analyzing section executes analysis of reflection light from a plurality of different positions on the user face, and
the light-reception-signal analyzing section acquires different pieces of bioanalysis information corresponding to positions.

(11) The information processing apparatus according to any of (1) to (9), in which
the light-reception-signal analyzing section executes analysis of reflection light from a plurality of different positions on the user face, and
the light-reception-signal analyzing section acquires highly precise bioanalysis information by complementarily using information acquired from a plurality of different positions.

(12) The information processing apparatus according to any of (1) to (11), further including:
a high-precision affect analyzing section that receives, as inputs, facial-expression analysis information generated by the facial-expression analyzing section, and bioanalysis information generated by the biometric-signal analyzing section, the high-precision affect analyzing section generating high-precision affect information representing a highly precise user emotion by using the facial-expression analysis information and the bioanalysis information that are received as the inputs.

(13) The information processing apparatus according to (12), in which the high-precision affect analyzing section executes an affect analysis process by referring to a learning model stored on a storage section.

(14) The information processing apparatus according to (13), in which the learning model is a model in which feature data that corresponds to a plurality of different affect states is associated, and the feature data includes feature data of facial-expression information and feature data of bioinformation.

(15) The information processing apparatus according to any of (12) to (14), further including:
a game control section that executes game control based on the high-precision affect information.

(16) The information processing apparatus according to any of (12) to (14), further including:
a facial-expression authenticity determining section that executes facial-expression authenticity determination based on the high-precision affect information.

(17) The information processing apparatus according to any of (1) to (16), further including:
an avatar control section that executes avatar control based on the facial-expression analysis information and the bioanalysis information.

(18) An information processing method executed at an information processing apparatus, in which
the information processing apparatus includes
a light-receiving section that receives reflection light of light emitted to a user face and
a light-reception-signal analyzing section that analyzes a light-reception signal of the light-receiving section,
the light-reception-signal analyzing section executes a facial-expression analysis process of generating facial-expression analysis information on the basis of the reflection light, and
the light-reception-signal analyzing section executes a biometric-signal analysis process of generating bioanalysis information on the basis of the reflection light.

(19) A program that causes information processing to be executed at an information processing apparatus, in which
the information processing apparatus includes
a light-receiving section that receives reflection light of light emitted to a user face, and
a light-reception-signal analyzing section that analyzes a light-reception signal of the light-receiving section, and
the program causes the light-reception-signal analyzing section to execute
a facial-expression analysis process of generating facial-expression analysis information on the basis of the reflection light, and
a biometric-signal analysis process of generating bioanalysis information on the basis of the reflection light.

Note that the series of processes explained in the specification can be executed by hardware, software, or a combined configuration of hardware and software. In a case where the processes are executed by software, a program having a process sequence recorded therein can be installed on a memory in a computer incorporated into dedicated hardware and executed thereon, or the program can be installed on a general-purpose computer that can execute various types of processes and executed thereon. For example, the program can be recorded in advance on a recording medium. Other than being installed from the recording medium onto a computer, the program can be received via a network such as a LAN (Local Area Network) or the Internet and installed on a recording medium such as a built-in hard disk.

In addition, various types of processes described in the specification may be executed not only in a time series according to the descriptions, but also in parallel or separately as necessary or according to the processing capability an apparatus that executes the processes. In addition, in the present specification, a system is a logical set configuration of a plurality of apparatuses, but is not limited to one having apparatuses of individual configurations that are located in a single housing.

INDUSTRIAL APPLICABILITY

As explained above, according to the configuration of one embodiment of the present disclosure, a configuration that analyzes reflection light of light emitted to a user face and executes both facial-expression analysis and biometric-signal analysis together is realized.

Specifically, for example, the configuration has a light-receiving section that receives reflection light of light emitted to a user face, and a light-reception-signal analyzing section that analyzes a light-reception signal of the light-receiving section. The light-reception-signal analyzing section has a facial-expression analyzing section that analyzes user-skin-surface reflection light and generates facial-expression analysis information, and a biometric-signal analyzing section that analyzes subepidermal reflection light and generates bioanalysis information. The light-reception signal of the light-receiving section includes skin-surface reflection light and subepidermal-tissue reflection light, and the facial-expression analyzing section extracts a low frequency component from the light-reception signal, acquires the skin-surface reflection light, and executes facial-expression analysis. The biometric-signal analyzing section extracts a high frequency component from the light-reception signal, acquires the subepidermal-tissue reflection light, and executes a biometric-signal analysis process.

According to this configuration, a configuration that analyzes reflection light of light emitted to a user face and executes both facial-expression analysis and biometric-signal analysis together is realized.

REFERENCE SIGNS LIST

10: User
100: Information processing apparatus
101: Light-emission control section
102: Light-emitting section
103: Light-receiving section
104: Light-reception-signal analyzing section
201: Input section
210: Facial-expression analyzing section
211: Low-frequency-component extracting section
212: A/D converting section
213: Facial-expression-analysis-result generating section
214: Facial-expression-analysis-information storage section
220: Biometric-signal analyzing section
221: High-pass filter (high-frequency-component extracting section)
222: Amplifying section 223: A/D converting section
224: Noise removing section
225: Biometric-signal-analysis-result generating section
226: Biometric-signal-analysis-information storage section
230: High-precision affect analyzing section
231: High-precision affect-analysis-information storage section
401: Learner
421: Learner
450: Learner
470: Spirit-analysis information storage section
480: Spirit determining section
501: CPU
502: ROM
503: RAM
504: Bus
505: Input/output interface
506: Input section
507: Output section
508: Storage section
509: Communication section
510: Drive
511: Removable medium

The invention claimed is:

1. An information processing apparatus, comprising:
a light-emitting section configured to emit light to a user face;
a light-receiving section configured to:
  receive first reflection light based on the light emitted to the user face; and
  output a light-reception signal based on the received first reflection light; and
a light-reception-signal analyzing section configured to analyze the light-reception signal of the light-receiving section, wherein
  the light-reception-signal analyzing section includes:
    a facial-expression analyzing section configured to generate facial-expression analysis information based on the first reflection light; and
    a biometric-signal analyzing section configured to:
      extract a high frequency component from the light-reception signal of the light-receiving section;
      acquire subepidermal-tissue reflection light based on the high frequency component;
      execute a biometric-signal analysis process based on the subepidermal-tissue reflection light; and
      generate first bioanalysis information based on the biometric-signal analysis process.

2. The information processing apparatus according to claim 1, wherein
the light-reception signal of the light-receiving section includes skin-surface reflection light and the subepidermal-tissue reflection light,
the facial-expression analyzing section is further configured to:
  extract a low frequency component from the light-reception signal of the light-receiving section,
  acquire the skin-surface reflection light based on the extracted low frequency component, and
  execute facial-expression analysis process based on the acquired skin-surface reflection light.

3. The information processing apparatus according to claim 1, wherein
the facial-expression analyzing section includes a facial-expression analysis information storage section,
the facial-expression analysis information storage section is configured to store a learning model, and
the facial-expression analyzing section is further configured to execute a facial-expression analysis process based on the stored learning model.

4. The information processing apparatus according to claim 3, wherein
the learning model includes corresponding data of facial-expression labels and feature data of skin-surface reflection-light signals,
the skin-surface reflection-light signals are associated with skin-surface movements, and
the facial-expression labels correspond to a plurality of different facial expressions.

5. The information processing apparatus according to claim 1, wherein
the biometric-signal analyzing section includes a biometric-signal analysis information storage section,
the biometric-signal analysis information storage section is configured to store a learning model, and
the biometric-signal analyzing section is further configured to execute a bioanalysis process based on the stored learning model.

6. The information processing apparatus according to claim 5, wherein
the learning model includes corresponding data of feature data of subepidermal reflection-light signals,
the subepidermal reflection-light signals correspond to a plurality of different biological states, and
the feature data of the subepidermal reflection-light signals reflect subepidermal states.

7. The information processing apparatus according to claim 1, wherein the generated first bioanalysis information includes least one of a blood flow rate, a blood flow speed, a pulse wave, a blood pressure, a heart rate, a heart rate fluctuation, a blood oxygen concentration, or arterial oxygen saturation.

8. The information processing apparatus according to claim 1, wherein
the light-receiving section includes a plurality of sensors, and
each of the plurality of sensors is attached at a respective position of a plurality of positions of a head-mounted display.

9. The information processing apparatus according to claim 1, wherein the light-reception-signal analyzing section is further configured to execute analysis of second reflection light from a plurality of different positions on the user face.

10. The information processing apparatus according to claim 1, wherein
the light-reception-signal analyzing section is further configured to:
  execute analysis of second reflection light from a plurality of different positions on the user face; and
  acquire different pieces of second bioanalysis information corresponding to the plurality of different positions.

11. The information processing apparatus according to claim 1, wherein
the light-reception-signal analyzing section is further configured to:
  execute analysis of second reflection light from a plurality of different positions on the user face; and
  acquire second bioanalysis information by complementarily using information acquired from the plurality of different positions.

12. The information processing apparatus according to claim 1, further comprising:
a high-precision affect analyzing section configured to:
receive a first input and a second input, wherein the first input includes the facial-expression analysis information and the second input includes the first bioanalysis information; and
generate high-precision affect information based on the facial-expression analysis information and the first bioanalysis information.

13. The information processing apparatus according to claim 12, wherein
the high-precision affect analyzing section includes a high-precision affect analysis information storage section,
the high-precision affect analysis information storage section is configured to store a learning model, and
the high-precision affect analyzing section is further configured to execute an affect analysis process based on the stored learning model.

14. The information processing apparatus according to claim 13, wherein
the learning model is a model in which feature data that corresponds to a plurality of different affect states is associated, and
the feature data includes feature data of facial-expression information and feature data of bioinformation.

15. The information processing apparatus according to claim 12, further comprising a game control section configured to execute game control based on the high-precision affect information.

16. The information processing apparatus according to claim 12, further comprising a facial-expression authenticity determining section configured to execute facial-expression authenticity determination based on the high-precision affect information.

17. The information processing apparatus according to claim 1, further comprising an avatar control section configured to execute avatar control based on the facial-expression analysis information and the first bioanalysis information.

18. An information processing method, comprising:
emitting, by a light-emitting section, light to a user face;
receiving, by a light-receiving section, reflection light based on the light emitted to the user face;
outputting, by the light-receiving section, a light-reception signal based on the received reflection light;
analyzing, by a light-reception-signal analyzing section, the light-reception signal of the light-receiving section, wherein the light-reception-signal analyzing section includes a facial-expression analyzing section and a biometric-signal analyzing section;
executing, by the facial-expression analyzing section, a facial-expression analysis process to generate facial-expression analysis information, wherein the facial-expression analysis information is generated based on the reflection light;
extracting, by the biometric-signal analyzing section, a high frequency component from the light-reception signal of the light-receiving section;
acquiring, by the biometric-signal analyzing section, subepidermal-tissue reflection light based on the high frequency component;
executing, by the biometric-signal analyzing section, a biometric-signal analysis process based on the subepidermal-tissue reflection light; and
generating, by the biometric-signal analyzing section, bioanalysis information based on the biometric-signal analysis process.

19. A non-transitory computer-readable medium having stored thereon, computer executable instructions, which when executed by a computer, cause the computer to execute operations, the operations comprising:
emitting light to a user face;
receiving reflection light based on the light emitted to the user face;
outputting a light-reception signal based on the received reflection light;
analyzing the light-reception signal;
execute a facial-expression analysis process to generate facial-expression analysis information, wherein the facial-expression analysis information is generated based on the reflection light;
extracting a high frequency component from the light-reception signal;
acquiring subepidermal-tissue reflection light based on the high frequency component;
executing a biometric-signal analysis process based on the subepidermal-tissue reflection light; and
generating bioanalysis information based on the biometric-signal analysis process.

* * * * *